(12) United States Patent  
Tsukizawa et al.

(10) Patent No.: US 8,538,044 B2  
(45) Date of Patent: Sep. 17, 2013

(54) LINE-OF-SIGHT DIRECTION DETERMINATION DEVICE AND LINE-OF-SIGHT DIRECTION DETERMINATION METHOD

(75) Inventors: Sotaro Tsukizawa, Kanagawa (JP); Kensuke Maruya, Kanagawa (JP)

(73) Assignee: Panasonic Corporation, Osaka (JP)

( * ) Notice: Subject to any disclaimer, the term of this patent is extended or adjusted under 35 U.S.C. 154(b) by 340 days.

(21) Appl. No.: 13/121,220

(22) PCT Filed: Sep. 25, 2009

(86) PCT No.: PCT/JP2009/004853  
§ 371 (c)(1), (2), (4) Date: May 20, 2011

(87) PCT Pub. No.: WO2010/035472  
PCT Pub. Date: Apr. 1, 2010

(65) Prior Publication Data  
US 2011/0249868 A1    Oct. 13, 2011

(30) Foreign Application Priority Data  
Sep. 26, 2008    (JP) ................................. 2008-248877

(51) Int. Cl.  
*G06K 9/00* (2006.01)

(52) U.S. Cl.  
USPC ............ 381/117; 382/103; 382/104; 382/118

(58) Field of Classification Search  
USPC ................... 382/117–118, 103–104  
See application file for complete search history.

(56) References Cited

U.S. PATENT DOCUMENTS

| 5,926,655 | A  | * | 7/1999 | Irie et al. ........................ 396/51 |
| 7,580,545 | B2 | * | 8/2009 | Venkatesh ..................... 382/103 |
| 2002/0048456 | A1 | | 4/2002 | Ohtani |
| 2009/0304232 | A1 | | 12/2009 | Tsukizawa |

FOREIGN PATENT DOCUMENTS

| JP | 2-4313 | 1/1990 |
| JP | 4-242630 | 8/1992 |
| JP | 2002-119478 | 4/2002 |
| JP | 2005-66023 | 3/2005 |
| JP | 2008-126329 | 6/2008 |
| WO | 2008/007781 | 1/2008 |

\* cited by examiner

*Primary Examiner* — Ruiping Li  
(74) *Attorney, Agent, or Firm* — Greenblum & Bernstein, P.L.C.

(57) ABSTRACT

Provided are a line-of-sight direction determination device and a line-of-sight direction determination method capable of highly precisely and accurately determining a line-of-sight direction from immediately after start of measurement without indication of an object to be carefully observed and adjustment work done in advance. The line-of-sight direction determination device (100) comprises: a line-symmetric position determination unit (150) for determining that the corneal reflection image of a left eye or a right eye is located at a line-symmetric position with respect to the center line of the pupils of the right and left eyes; and a line-of-sight direction determination unit (170) for determining, from the line-symmetric position determination result, a line-of-sight direction at a specific position including the installation position of an imaging unit (111) or an irradiation unit (112) at the substantially same position as the imaging unit (111). The line-of-sight direction determination device (100) determines that the corneal reflection image is line symmetric and, from this line symmetry property, determines a specific line-of-sight direction.

7 Claims, 16 Drawing Sheets

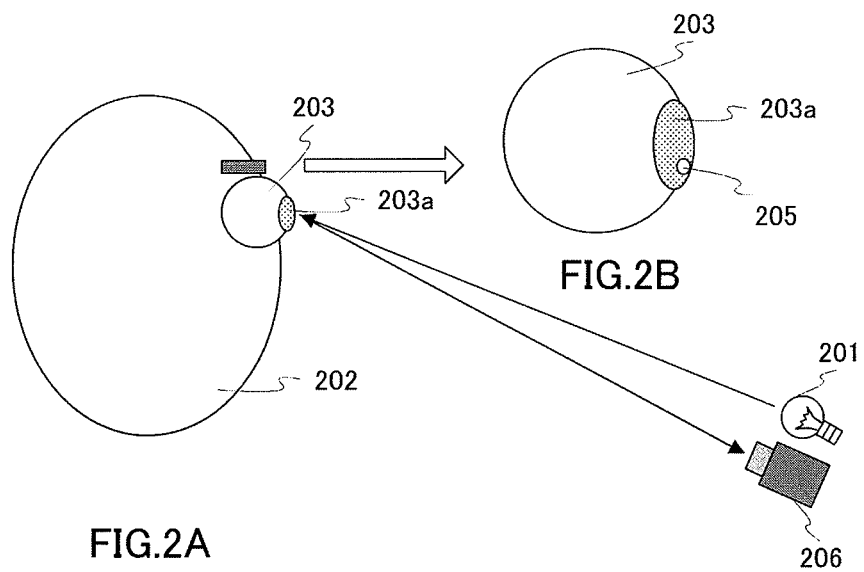
FIG.2A
FIG.2B
FIG.3

LINE-OF-SIGHT DIRECTION DETERMINATION DEVICE AND LINE-OF-SIGHT DIRECTION DETERMINATION METHOD

TECHNICAL FIELD

The present invention relates to a line-of-sight direction determining apparatus and a line-of-sight direction determining method for determining whether the direction of an imaged person's line of sight matches a predetermined direction.

BACKGROUND ART

A line-of-sight direction determining apparatus for determining the direction of a person's line of sight needs to represent a detected direction in coordinates in external space.

Patent literature 1 discloses a line-of-sight detecting apparatus that detects in advance the condition of the eyeball while looking at a specific direction and determines from that result whether or not the eyeball is looking at a specific direction. The apparatus disclosed in patent literature 1 attentively views an indicator in a finder and corrects the difference between the visual axis and the eye axis then.

Patent literature 2 discloses a driving condition detecting apparatus that observes the direction of a driver's line of sight over a long period of time during driving, and from its distribution determines a reference line-of-sight direction. The apparatus disclosed in patent literature 2 estimates a reference line-of-sight position from time series data.

Thus, conventionally, there are two categories of methods of line-of-sight direction determination. One is to specify or detect a target to attentively view and detect the condition of attentive viewing (e.g. apparatus disclosed in patent literature 1), and the other one is to determine the center of the direction of line of sight from the distribution of line of sight over a long period of time (e.g. apparatus disclosed in patent literature 2).

CITATION LIST

Patent Literature

PTL 1
Japanese Patent Application Laid-Open No. 1992-242630
PTL 2
Japanese Patent Application Laid-Open No. 2005-66023

SUMMARY OF INVENTION

Technical Problem

However, conventional line-of-sight direction determining apparatuses such as these have the following problems.

(1) The apparatus of patent literature 1 needs to specify a target to attentively view, and this involves a complex operation. Also, with automatic detection, it is difficult to judge whether a target is really looking. Either way a prior measurement process is required, and therefore convenience is not improved.

(2) The apparatus disclosed in patent literature 2 does not guarantee that the distribution of line of sight measured over a long period of time really is turned in the front direction. Furthermore, correction is possible only after a long period of time of measurement. That is to say, there is a problem that a long period of time of measurement is required and furthermore there is no guarantee that measured statistical results are constant and do not show individual variations, and therefore it is difficult to detect the line of sight shortly after measurement is started or guarantee the accuracy of measurement.

The present invention has been made in view of the above problems, and it is therefore an object of the present invention to provide a line-of-sight direction determining apparatus and a line-of-sight direction determining method whereby, without specifying a target to attentively view or involving a prior adjustment process, it is possible to detect the direction of line of sight shortly after measurement is started and accurately and correctly determine the direction of line of sight.

Solution to Problem

A line-of-sight direction determining apparatus adopts a configuration including: an imaging section that takes an image of a face including right and left eyes; an illuminating section that illuminates corneas of the right and left eyes using a light source; a pupil detecting section that detects a first coordinate and a second coordinate, the first coordinate and the second coordinate being a center coordinate of the pupil of one of the right and left eyes and a center coordinate of the pupil of the other one of the right and left eyes, respectively; a cornea reflection image detecting section that detects a third coordinate and a fourth coordinate, the third coordinate and the fourth coordinate being a center coordinate of a cornea reflection image of the light source on the cornea of one of the right and left eyes and a center coordinate of a cornea reflection image of the light source on the cornea of the other one of the right and left eyes, respectively; a line-symmetric position calculating section that calculates a perpendicular bisector of a first line segment connecting between the first coordinate and the second coordinate, and calculates a line-symmetric position coordinate being a position coordinate that is line-symmetric to the third coordinate with respect to the perpendicular bisector; and a line-of-sight direction determining section that calculates a coordinate distance between the fourth coordinate and the line-symmetric position coordinate, and, based on a comparison of the coordinate distance and a predetermined threshold, determines a direction of line of sight of the right and left eyes.

A line-of-sight direction determining method according to the present invention includes the steps of: taking an image of a face including right and left eyes, illuminating corneas of the right and left eyes using a light source; detecting a first coordinate and a second coordinate, the first coordinate and the second coordinate being a center coordinate of the pupil of one of the right and left eyes and a center coordinate of the pupil of the other one of the right and left eyes, respectively; detecting a third coordinate and a fourth coordinate, the third coordinate and the fourth coordinate being a center coordinate of a cornea reflection image of the light source on the cornea of one of the right and left eyes and a center coordinate of a cornea reflection image of the light source on the cornea of the other one of the right and left eyes, respectively; calculating a perpendicular bisector of a first line segment connecting between the first coordinate and the second coordinate, and calculating a line-symmetric position coordinate being a position coordinate that is line-symmetric to the third coordinate with respect to the perpendicular bisector; and calculating a coordinate distance between the fourth coordinate and the line-symmetric position coordinate, and, based on a comparison of the coordinate distance and a predetermined threshold, determining a direction of line of sight of the right and left eyes.

Advantageous Effects of Invention

According to the present invention, by determining whether images reflected on the corneas of the right and left eyes are in positions line-symmetric to the center line of the pupils of the right and left eyes and determining the direction of line of sight in a specific position from the determination result, it is not necessary to specify a target to attentively view or perform adjustment process in advance upon determining the direction of line of sight, and consequently it is possible to improve convenience. Furthermore, characteristics that are common between people are used, so that the reliability of determination results is high, and, compared to a technique involving statistic processing, it is possible to determine the direction of line of sight accurately. For the same reason, it is possible to guarantee that the direction of line of sight that is determined is the correct direction of line of sight, so that, unlike heretofore, it is not necessary to perform measurement over a long period of time. Furthermore, it is possible to detect the direction of line of sight directly from a photographed image, so that it is possible to determine the direction of line of sight shortly after measurement is started.

In addition to the above advantages, there are the following advantages.

That is to say, it is possible to correct the offset of the direction of line of sight detected automatically, without looking at a specific target of attentive viewing. Furthermore, since attentive viewing is not necessary, it is possible to lighten the process and prevent determination errors. This leads to increasing the opportunities of correction. Furthermore, looking at the direction of the camera for only one frame is sufficient, so that correction is possible at high likelihood.

BRIEF DESCRIPTION OF DRAWINGS

FIGS. 2A and 2B explain a line-of-sight direction determining method of a line-of-sight direction determining apparatus according to embodiment 1;

FIG. 3 explains a line-of-sight direction determining method of a line-of-sight direction determining apparatus according to embodiment 1;

DESCRIPTION OF EMBODIMENTS

Embodiments of the present invention will be described in detail below with reference to the accompanying drawings.

(Embodiment 1)

The present invention relates to a line-of-sight direction determining apparatus that determines the center of the iris or pupil and an image of lighting reflected on the cornea, from an image of a face taken by an imaging apparatus with an illuminating means, and, from their line-symmetry, determines the direction of a subject's line of sight. Determining the direction of line of sight here refers to determining whether a subject's line of sight is turned in a specific direction. This specific direction does not necessarily refer to a single direction and may encompass a plurality of directions.

With embodiment 1 of the present invention, a line-of-sight direction determining apparatus will be described that determines the center of the iris or pupil and an image of lighting reflected on the cornea, from an image of a face taken by an imaging apparatus with an illuminating means, and, from their line-symmetry, determines the direction of a subject's line of sight.

Figure 1:
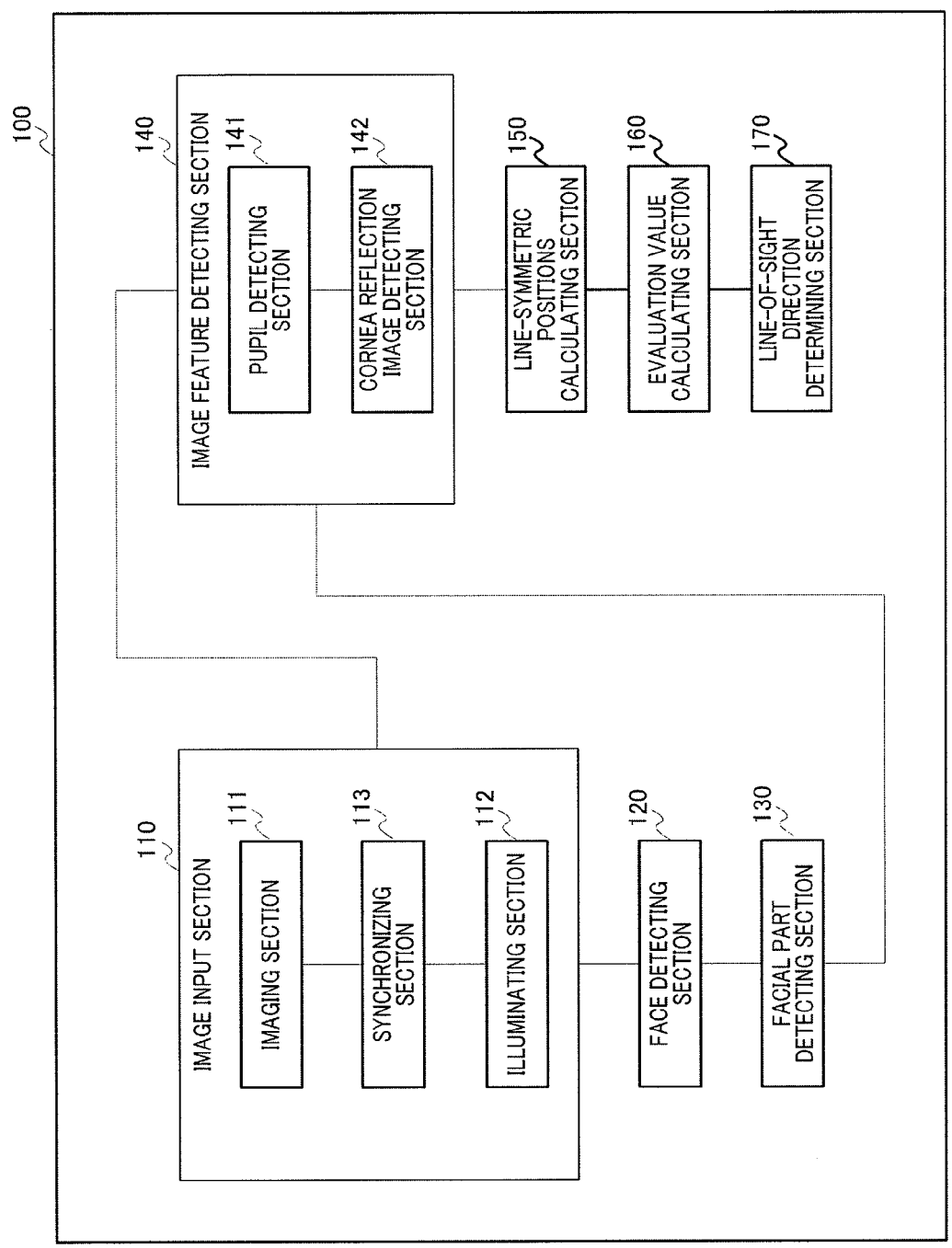
FIG. 1 is a block diagram showing a configuration a line-of-sight direction determining apparatus according to embodiment 1 of the present invention.

FIG. 1 is a block diagram showing a configuration a line-of-sight direction determining apparatus according to embodiment 1 of the present invention. The present embodiment is an example of applying a line-of-sight direction determining method of the present invention to a warning apparatus that is provided in the interior of a car and that detects the direction of a driver's line of sight and issues a warning when the drives does not look at the front for a long period of time.

As shown in FIG. 1, line-of-sight determining apparatus 100 is applicable to, for example, devices to present information, such as a car navigation system, television and speaker, devices to monitor safety conditions such as a driver assisting camera and surveillance camera, devices to record images such as a still camera and video camera, and devices that require information as to what a user or imaged person is looking at such as a life assistance device like a robot.

Line-of-sight direction determining apparatus 100 is configured with image input section 110, face detecting section 120, facial part detecting section 130, image feature detecting section 140, line-symmetric position calculating position 150, evaluation value calculating section 160, and line-of-sight direction determining section 170.

Image input section 110 outputs an image photographed by imaging section 111, to face detecting section 120 (described later).

Image input section 110 has imaging section provided in the front of the driver's sheet such as above the steering wheel or on top of the dashboard, that is, provided in a position from which a driver can be photographed, illuminating section 112 that illuminates the driver's face, and synchronizing section 113 that makes imaging section 11 and illuminating section 112 synchronized.

Imaging section 111 is provided with an image sensor such as a CCD (Charge Coupled Device) and CMOS (Complementary Metal Oxide Semiconductor) and acquires an image according to a synchronizing signal received as input from synchronizing section 113.

In the following descriptions, in a photographed face image, the X axis defines the lateral directions in the image, the Y axis defines the vertical directions in the image, and one pixel defines one coordinate point.

Illuminating section 112 has, although not visible, a near infrared LED that is sensitive in imaging section 111, and emits light in accordance with a synchronization signal from synchronizing section 113.

Synchronizing section 113 outputs a synchronizing signal to imaging section 111 and illuminating section 112, during the period of time from the start to end of exposure in imaging section 111.

Face detecting section 120 detects a face image, which is an image of a person's face, from an image received as input from image input section 110, and outputs the face image to facial part detecting section 130.

Facial part detecting section 130 detects facial parts such as the outer corner of the eye, the inner corner of the eye, the center of the iris, the nostrils, the corner of the mouth, the corner of the eyebrow, and outputs the coordinates of a plurality of points defining the contour of each facial part, to image feature detecting section 140.

Image feature detecting section 140 has iris detecting section 141 that detects the irises in a face image, and cornea reflection image detecting section 142 that detects an image of illuminating section 112 reflected on the cornea in a face image. A "cornea reflection image" refers to an image reflected on the surface of the cornea, commonly referred to as a "Purkinje image."

From the face image received as input from image input section 110 and the facial part coordinates received as input from facial part detecting section 130, pupil detecting section 141 detects the pupils of the right and left eyes and outputs the center coordinates of the right and left pupils, to line-symmetric position calculating position 150.

From the face image received as input from image input section 110 and the facial part coordinates received as input from facial part detecting section 130, cornea reflection image detecting section 142 detects the cornea reflection images of illuminating section 112 in the right and left eyes, and outputs the center coordinates of the right and left pupils to line-symmetric position calculating position 150.

From the coordinates of the centers of the right and left eye pupils received as input from image feature detecting section 140 and the center coordinates of the cornea reflection images, line-symmetric position calculating position 150 calculates a position that is line-symmetric to the center of the cornea reflection image in one of the right and left eyes, and outputs that line-symmetric position's coordinates and the coordinates of the center of the cornea reflection image in the other eye, to evaluation value calculating section 160. Line symmetry here refers to a state of line symmetry with respect to the perpendicular bisector of line segments starting from the endpoints at the centers of the right and left pupils.

From the projection coordinates received as input from line-symmetric position calculating position 150, the center coordinates of cornea reflection images receives as input from image feature detecting section 140, and the line-symmetric position coordinates, evaluation value calculating section 160 calculates a line symmetry evaluation value to evaluate the line symmetry of the cornea reflection images and outputs that evaluation value to line-of-sight direction determining section 170.

From the line symmetry evaluation value received as input from evaluation value calculating section 160, line-of-sight direction determining section 170 determines the line symmetry between the right and left cornea reflection images, and, if these are line-symmetric, determines that the direction of the subject's line of sight is turned in the direction of the camera, or, if these are not line-symmetric, determines that the direction of the subject's line of sight is not turned in the direction of the camera, and outputs the determination result to a warning apparatus (not shown). The warning apparatus (not shown) issues a warning when a determination result shows that the subject has not looked at the camera's direction for a long period of time. This warning may be given by, for example, displaying a warning message, displaying a sound/speech message by means of a sound/speech synthesis LSI, emitting light from an LED, producing a sound from a speaker or the like or by combining these.

The functions of these components are implemented by executing a control program on a microcomputer. Line-of-sight direction determining apparatus 100 has a CPU, which is a control section, a ROM in which a control program is recorded, and a RAM which is provided to execute a program, a camera which is an imaging apparatus, and a display section which is a display/warning apparatus, and the control section controls the operations of individual components of line-of-sight direction determining apparatus 100. Parts in FIG. 1 are shown expressly as blocks to perform line-of-sight direction determining processes executed in the control section.

The operations of line-of-sight direction determining apparatus 100 configured as above will be described now.

The basic idea of the line-of-sight direction determining method will be explained first.

FIG. 2 to FIG. 4 explain the line-of-sight direction determining method of line-of-sight direction determining apparatus 100.

As shown in FIG. 2A, projector 201 (illuminating section 112 in FIG. 1) illuminates eyeball 203 of face 202. Camera 206 (imaging section 111 in FIG. 1) acquires cornea reflection image 205, reflected on cornea 203a of eyeball 203. As shown in FIG. 2B, by the illumination of light from projector 201, cornea reflection image 205 appears on cornea 203a of eyeball 203.

Line-of-sight direction determining apparatus 100 detects cornea reflection images 205 in the right and left eyes by utilizing the bilateral symmetry of the face. That is to say, the positions of cornea reflection image 205 in the right and left eyes are calculated, and whether the calculated positions of the cornea reflection images are line-symmetric positions between the right and left eyes.

As shown in FIG. 3, cornea reflection images 205 of projector 201 are acquired from the right and left eyes, and, based on the symmetry of cornea reflection images 205 with respect to pupil 204, detection is made when the direction of projector 201 is being looked at. Furthermore, by checking the bilateral symmetry of the positions of cornea reflection images of projector 201, whether or not the subject is looking at the direction of camera 206 is determined.

Figure 4A:
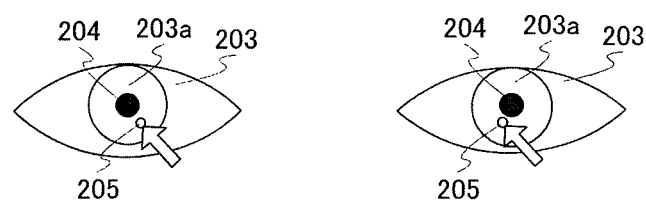
FIGS. 4A and 4B explain a line-of-sight direction determining method of a line-of-sight direction determining apparatus according to embodiment 1.
Figure 4B:
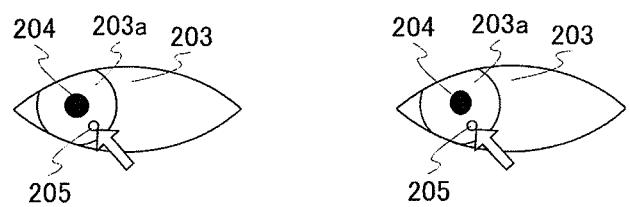

To be more specific, as shown in FIG. 4A, if the subject is looking at the direction of camera 206 or projector 20, the positions of cornea reflection images 205 are bilaterally symmetric. Furthermore, as shown in FIG. 4B, if the subject is not looking at the direction of camera 206 or projector 201, the positions of cornea reflection images 205 are bilaterally asymmetric.

The line-of-sight direction determining method will be explained in detail next.

[Algorithm]
1. Detect the pupils and cornea reflection images
2. Project one reflected image in a position symmetric to the perpendicular bisector of the right and left pupils
3. Detect the offset between the projected reflected image and the other reflected image
4. When the amount of offset is equal to or less than a threshold, the direction of line of sight then is determined to be the camera's direction FIG. 5 explains a line-of-sight direction determining algorithm, where FIG. 5A shows a face image and FIG. 5B shows a face image and a perpendicular bisector of a line segment connecting between the right and left eyes calculated based on the face image.

Figure 5A:
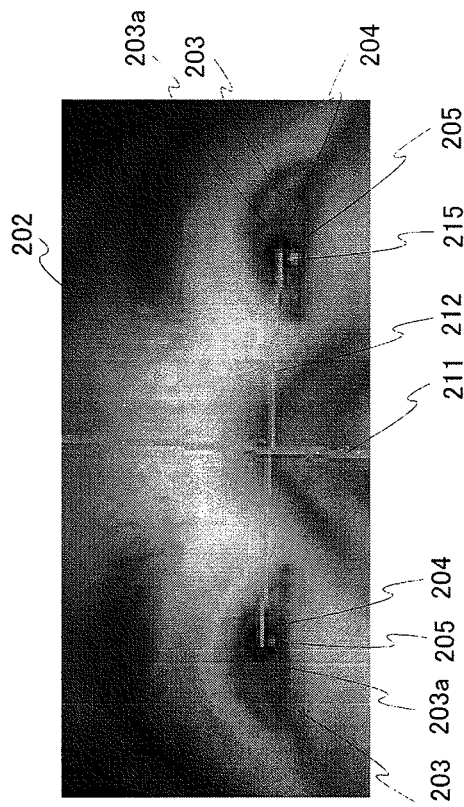
FIGS. 5A and 5B explain a line-of-sight direction determining algorithm of a line-of-sight direction determining apparatus according to embodiment 1.

As shown in FIG. 5A, from face image 202, eyeballs 203, pupils 204 of the right and left eyes, and cornea reflection images 205 in the right and left eyes are detected from face image 202.

Figure 5B:
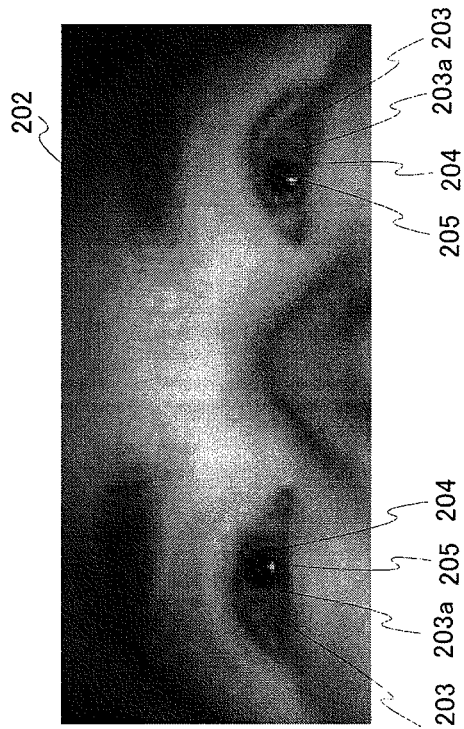

As shown in FIG. 5B, the present algorithm projects one reflected image in a position symmetric with respect to perpendicular bisector 211 of the right and left pupils. The other cornea reflection image 205 projected on eyeball 203 is referred to as "cornea-projected image 215" (see projection line 212). Here, cornea reflection image 205 in the right eye is projected on the left eye, so that, in the left eye, left eye cornea reflection image 205 and cornea-projected image 215 that is projected, are placed close.

The present algorithm detects the offset between left eye cornea reflection image 205 and cornea-projected image 215 that is projected. If the amount of this offset is equal to or lower than a threshold, the direction of line of sight then is determined to be the direction of the camera. The means for implementing the present algorithm will be described later using the line-of-sight direction determining process flow of FIG. 6.

Thus, by examining whether or not the coordinate positions of the cornea reflection images in the right and left eyes are line-symmetric with respect to perpendicular bisector 211, the direction of line of sight can be determined.

Figure 6:
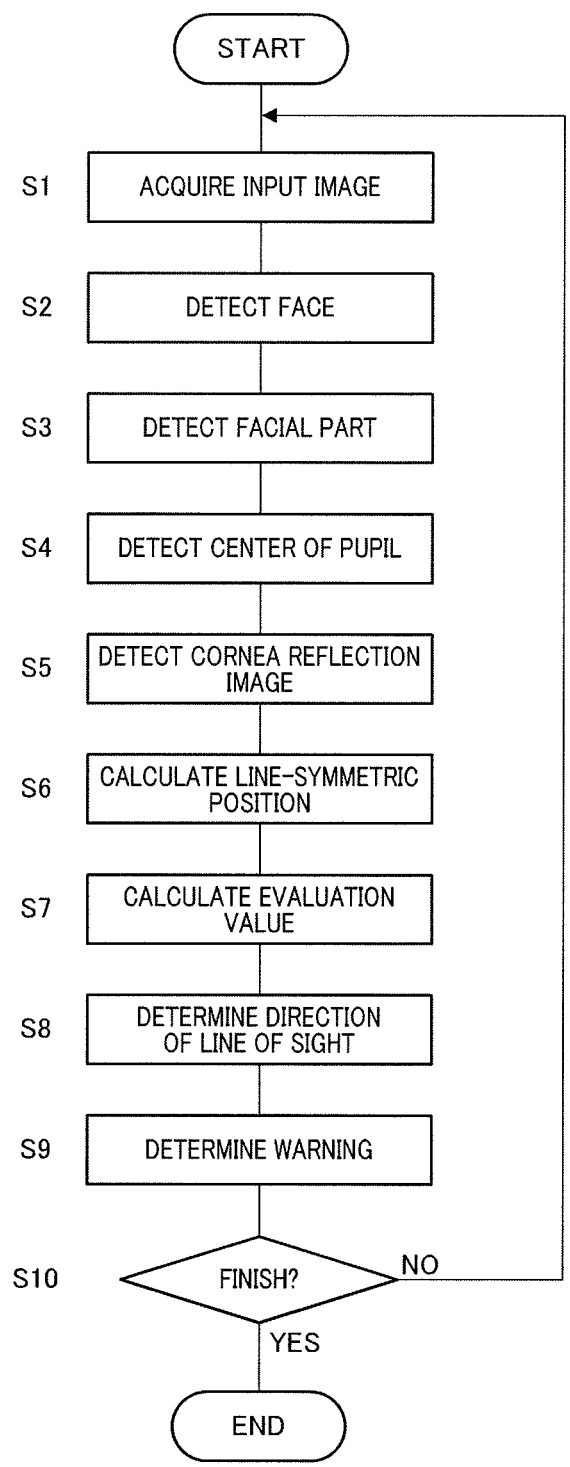
FIG. 6 is a flowchart showing a line-of-sight direction determining process of a line-of-sight direction determining apparatus according to embodiment 1.
Figure 7:
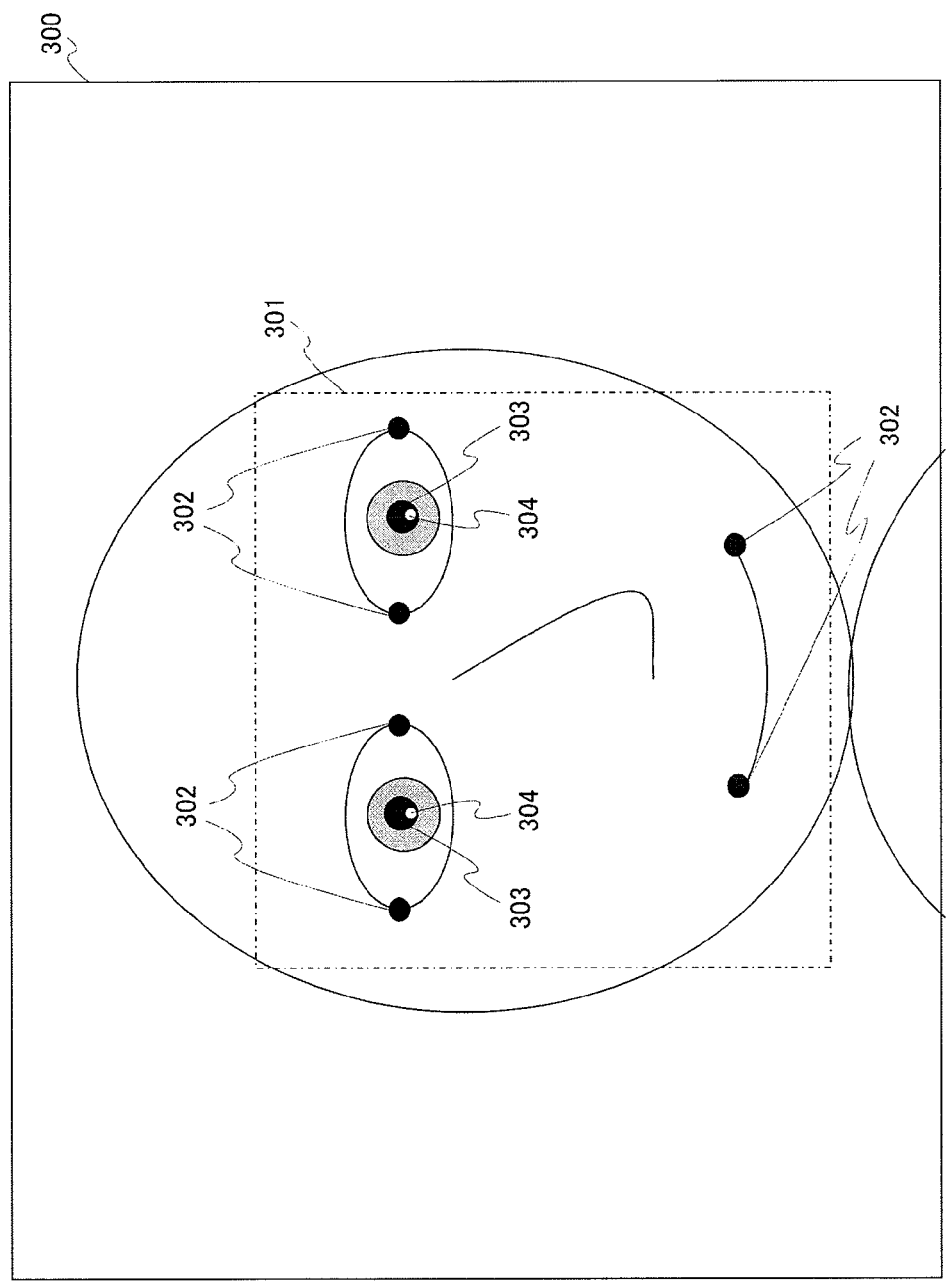
FIG. 7 shows an example of an input image received as input in a line-of-sight direction determining apparatus according to embodiment 1.

FIG. 6 is a flowchart of line-of-sight direction determining processing in line-of-sight direction determining apparatus 100. FIG. 7 shows a face image received as input in line-of-sight direction determining apparatus 100.

In FIG. 6, when the program starts, image input section 110 starts an imaging operation. The imaging operation may be started manually by a person or may be started by line-of-sight direction determining apparatus 100 using some sort of external signal as a trigger.

In step S1, image input section 110 acquires face image 300 of FIG. 7 from imaging section 111 synchronized with illuminating section 112 by synchronization section 113 on a regular basis.

For example, for image input section 110, a digital camera provided with a CMOS image sensor and lens, and a sensor configured with a projector provided with a near infrared LED are assumed, and, by this means, an image in PPM (Portable Pix Map file format) format taken in synchronization with the projector is stored temporarily in an image storing section inside image input section 110 (for example, PC memory space).

An image that is stored on a temporary basis this way is input in face detection section in PPM format.

Here, illuminating section 112 is a synchronized pulse drive near infrared LED projector that lights on in synchronization over the exposure period of imaging section 111. Despite this synchronized pulse drive, the light may be constantly on if the amount of light acquired is enough for imaging.

In step S2, face detecting section 120 perform a process of detecting face area 301 in face image 300 received as input from image input section 110.

In the face area detection, for example, an image to show features is extracted from an input image, and, by comparing this extracted feature image and a feature image showing a face area that is prepared in advance, detects an image showing high similarity to the compared image.

Similarity is determined by comparing the Gabor features of an average face and the Gabor features extracted from a scanned input image, and uses the reciprocal of the absolute value of the difference.

In this case, compared to a template prepared in advance, the area showing the highest correlation in face area 301 in FIG. 7 is searched for in an image.

Face area 301 can be detected by, for example, detecting flesh colors in an image, detecting ovals, or by using a statistic pattern recognition technique. Besides, any technology or method may be used as long as the above face detection is possible.

In step S3, facial part detecting section 130 performs a process of detecting facial part set 302 including the corner of the mouth, the outer corner of the eye, the inner corner of the eye and so on, in a search range of face area 301 in face image 300 received as input from face detecting section 120.

In the facial part detection, for example, the endpoints of facial parts such as the corner of the mouth, the outer corner of the eye, and the inner corner of the eye, and the two-dimensional coordinates of the nostril, are detected using, for example, a separability filter.

Furthermore, it is equally possible to make a learning device learn in advance the relationships between a plurality of face images and the positions of facial parts corresponding to the face images, and, when face image 300 is input in the learning device, detect places of high likelihoods as facial parts, or search for facial parts in face image 300 using a regular facial part template.

In step S4, pupil detecting section 141 detects the center coordinates of pupils 303 in FIG. 3, in the eye areas detected in the facial part set detection in above step S3.

The center coordinates of a pupil in a face image are extracted by for example, applying a circle separability filter to an eye area detected by the facial part set detection in above step S3 including the inner corner of the eye and the outer corner of the eye, and extracts the center coordinates of a circle having maximum brightness as the center coordinates of the pupil.

Then, taking into account the eyelid detected by edge detection using a Sobel filter or by binarizing brightness using Ohtsu's method, only the inner area sandwiched between the upper and lower eyelids is made the detection target range.

Furthermore, in an area including the outer corner of the eye and the inner corner of the eye, a sum of brightness is determined in the lateral direction and in the vertical direction, and the point where the sum of brightens in the vertical direction and the sum of brightens in the lateral direction are small, may be determined as the center of the pupil.

Furthermore, the target of detection does not necessarily have to be the pupil and may be the center of the iris, the center of the cornea, and so on.

Besides, any technology or method of detection may be used as long as the center coordinates of the pupil can be detected.

In step S5, cornea reflection image detecting section 142 detects the center coordinates of cornea reflection image 304 of FIG. 7 in the eye area detected in the facial part set detection in above step S3.

As for the center coordinates of a cornea reflection image, for example, by calculating a brightness histogram with respect to an area around the center of the pupil detected in above step S4, the centroid of the coordinates of the maximum brightness pixel can be detected as the center coordinates of a cornea reflection image. The centroid of the pixels of the highest several percents in a histogram (one percent, for example) may be acquired as well.

If the maximum brightens then is lower than a predetermined threshold, this is decided to indicate that there are no cornea reflection images, and the determining process is quit and returns to above step S1. If the number of pixels to show the maximum brightness is greater than a predetermined threshold, this is decided to indicate that a cornea reflection image shows a reflection of a different object from illuminating section 112, and the determining process is quit and returns to above step S1.

In step S6, line-symmetric position calculating position 150 calculates the perpendicular bisector of the line segment connecting between the center coordinates of pupil 303 received as input from image feature detecting section 140 and the center coordinates of cornea reflection image 304, and calculates the center coordinates of a line-symmetric position of one of the right and left cornea reflection images with respect to the calculated perpendicular bisector.

Figure 8A:
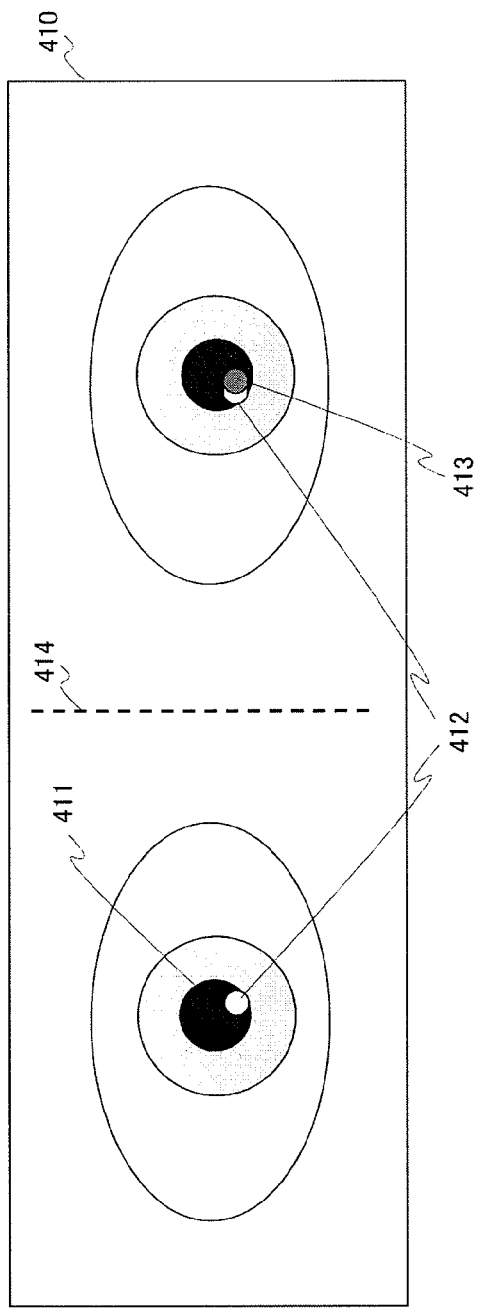
FIGS. 8A and 8B show examples of image features used in a line-of-sight direction determining apparatus according to embodiment 1.
Figure 8B:
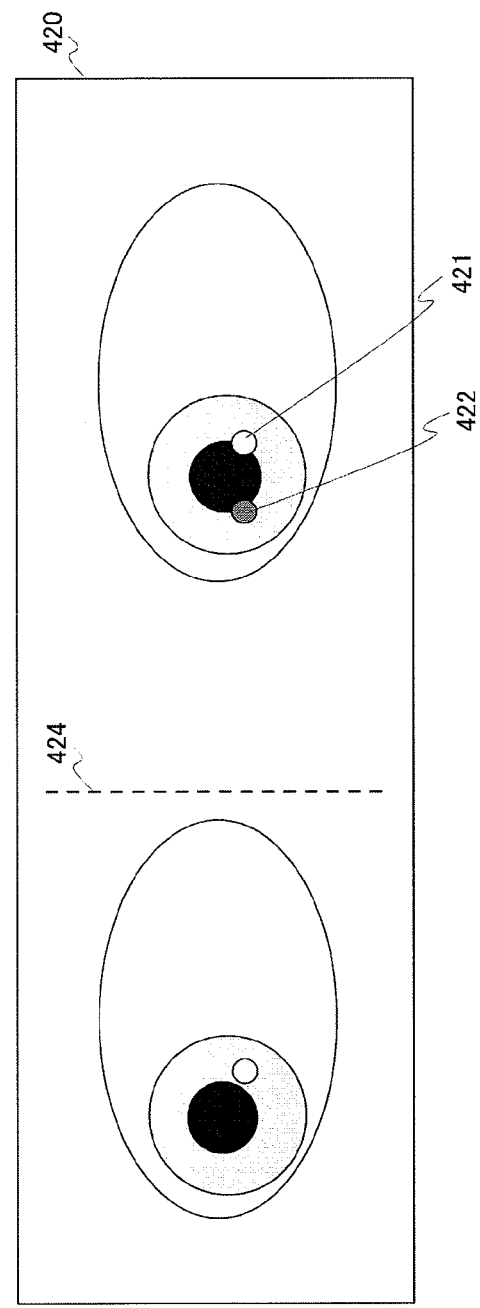

FIG. 8 shows examples of image features used in line-of-sight direction determining apparatus 100, where FIG. 8A shows image 410 when the line of sight matches the direction of camera 206 and FIG. 8B shows image 420 when the line of sight does not match the direction of camera 206.

In FIG. 8A, pupils 411 are the same as pupils 303 in FIG. 7, and cornea reflection images 412 are the same as cornea reflection images 304 in FIG. 7.

In FIG. 8, line-symmetric position calculating position 150 calculates perpendicular bisector 414 of the line segment connecting between the center coordinates of pupils 411 of the right and left eyes according to following equation 1.

(Equation 1)

$$\frac{-x_r + x_l}{y_r - y_l} x + y - \frac{y_r + y_l}{2} - \frac{a(x_r + x_l)}{2} = 0 \quad [1]$$

where the coordinates of the right eye pupil are (xr, yr), and the coordinates of the left eye pupil are (xl, yl).

Next, with respect to perpendicular bisector 414 represented by equation 1, a line-symmetric position of the center coordinates of cornea reflection image 304 in one of the right and left eyes is calculated according to equation 2. Note that equation 2 represents a line-symmetric position of the center coordinates of the right eye cornea reflection image, and the coordinates of that line-symmetric position are represented by (xs, ys).

(Equation 2)

$$x_s = x_r - \frac{2a(ax_r + y_r + b)}{a^2 + 1} \quad [2]$$

$$y_s = y_r - \frac{2(ax_r + y_r + b)}{a^2 + 1}$$

where a and b are both represented by following equation 3.

(Equation 3)

$$a = \frac{-x_r + x_l}{y_r - y_l} \quad [3]$$

$$b = -\frac{y_r + y_l}{2} - \frac{a(x_r + x_l)}{2}$$

In step S7, evaluation value calculating section 160 calculates the line symmetry of the positions of the right and left cornea reflection images from the center coordinates of cornea reflection images 304 received as input from image feature detecting section 140 and the line-symmetric position received as input from line-symmetric position calculating position 150, in the form of line symmetry evaluation value V represented by equation 4.

(Equation 4)

$$V = \frac{1}{(x_s - x_l)^2 + (y_s - y_l)^2 + 1} \quad [4]$$

As shown in image 410 of FIG. 8(a), for example, when the line of sight is turned in the direction of camera 206, line-symmetric position 424 of one of the right and left cornea reflection images is in a close position to the other cornea reflection image, so that line symmetry evaluation value V assumes a large value. However, as shown in image 410 of FIG. 8(b), for example, when the line of sight is not turned in the direction of camera 206, line-symmetric position 422 of one of the right and left cornea reflection images is in a distant position from the other cornea reflection image 421, so that the line symmetry evaluation value assumes a small value.

Line symmetry evaluation value V does not necessarily have to be a value represented by equation 4, and may be a greater evaluation value when line-symmetric position 422 of one of the right and left cornea reflection images and the other cornea reflection image 421 are closer.

In step S8, line-of-sight direction determining section 170 determines whether or not the direction of line of sight matches a specific direction from the line-symmetry evaluation value received as input from evaluation value calculating section 160. For example, when a line symmetry evaluation value is equal to or greater than a predetermined threshold, the direction of line of sight is determined to be turned in a specific direction.

It is also possible to record evaluation values over a certain period of time and determine that the direction of line of sight is turned in a specific direction when the average value equals or exceeds a threshold. The specific direction refers to the direction of image input section 110.

Besides, any technology or method of determination may be used as long as the above line-of-sight direction determination is possible.

In step S9, when the line of sight is determined not to be turned in the front direction in line-of-sight direction determining section 170, a warning apparatus (not shown) increments the warning count by one, the warning count showing the number of times the direction of line of sight is determined not to be directed in the front. When N exceeds a predetermined threshold, it is decided that the direction of line of sight is not directed in the front for a long period of time, and a warning is issued.

When the direction of line of sight is determined to be directed in the front, the warning count is made zero. The warning count is zero in its initial condition.

In step S10, a termination decision is made. A termination decision may be made by means of a terminating command received as input manually, or may be performed by line-of-sight direction determining apparatus using some type of external signal as a trigger.

If as a result of a termination decision the process is going to be finished, the line-of-sight direction determining operation of line-of-sight direction determining apparatus 100 is finished. When the line-of-sight determination is not finished in above step S10, the operation returns to above step S1.

As explained above in detail, line-of-sight direction determining apparatus 100 of the present embodiment has line-symmetric position determining section 150 that detects whether a cornea reflection image in the left eye or right eye is in a position line-symmetric position with respect to the center line of the pupils of the right and left eyes, and line-of-sight direction determining section 170 that determines the direction of line of sight in a specific position including the position where imaging section 111 is provided, or the position of illuminating section 112 provided in virtually the same position, determines the line symmetry of cornea reflection images and determines a specific line-of-sight direction from that line symmetry, so that it is possible to determine the direction of line of sight shortly after measurement is started and accurately and correctly determine the direction of line of sight, without specifying a specific target to attentively view or involving a prior adjustment process.

With conventional examples, when the positional relationship between the pupil and the cornea reflection images, the calculation is performed with respect to one eye. Even when both eyes are used, this is only to stabilize the line of sight, and, unlike the present invention, there is no example of use in detection of line of sight in a specific direction. With conventional examples, in order to detect a specific line-of-sight direction, it is necessary to detect or specify a target to attentively view and make estimation from statistics of detection results over quite a few seconds. By this means, the direction of line of sight can be determined accurately and correctly.

By contrast with this, the present embodiment determines whether the cornea reflection images in the left eye and the right eye are in line-symmetric positions with respect to the center line of the right and left eye pupils. The pupils and cornea reflection images have features that can be detected reliably from low resolution photographed images, so that the direction of line of sight can be determined reliably. The bilateral symmetry of cornea reflection images does not vary between individuals and can be used conveniently without involving a prior adjustment process. Furthermore, there are advantages that determination is possible using only one image, so that it is possible to determine the direction of line of sight shortly after measurement is started, and that the direction of line of sight can be determined even in a situation of looking at a specific direction for only a very short period of time. Furthermore, the present embodiment has evaluation value calculation section 160 that calculates an evaluation value to show the line symmetry of the right and left cornea reflection images, and line-of-sight direction determining section 170 first determines the line symmetry of the right and left cornea reflection images based on that evaluation value and then determines a specific line-of-sight direction next, so that even more accurate line-of-sight direction determination is possible.

(Embodiment 2)

Figure 9:
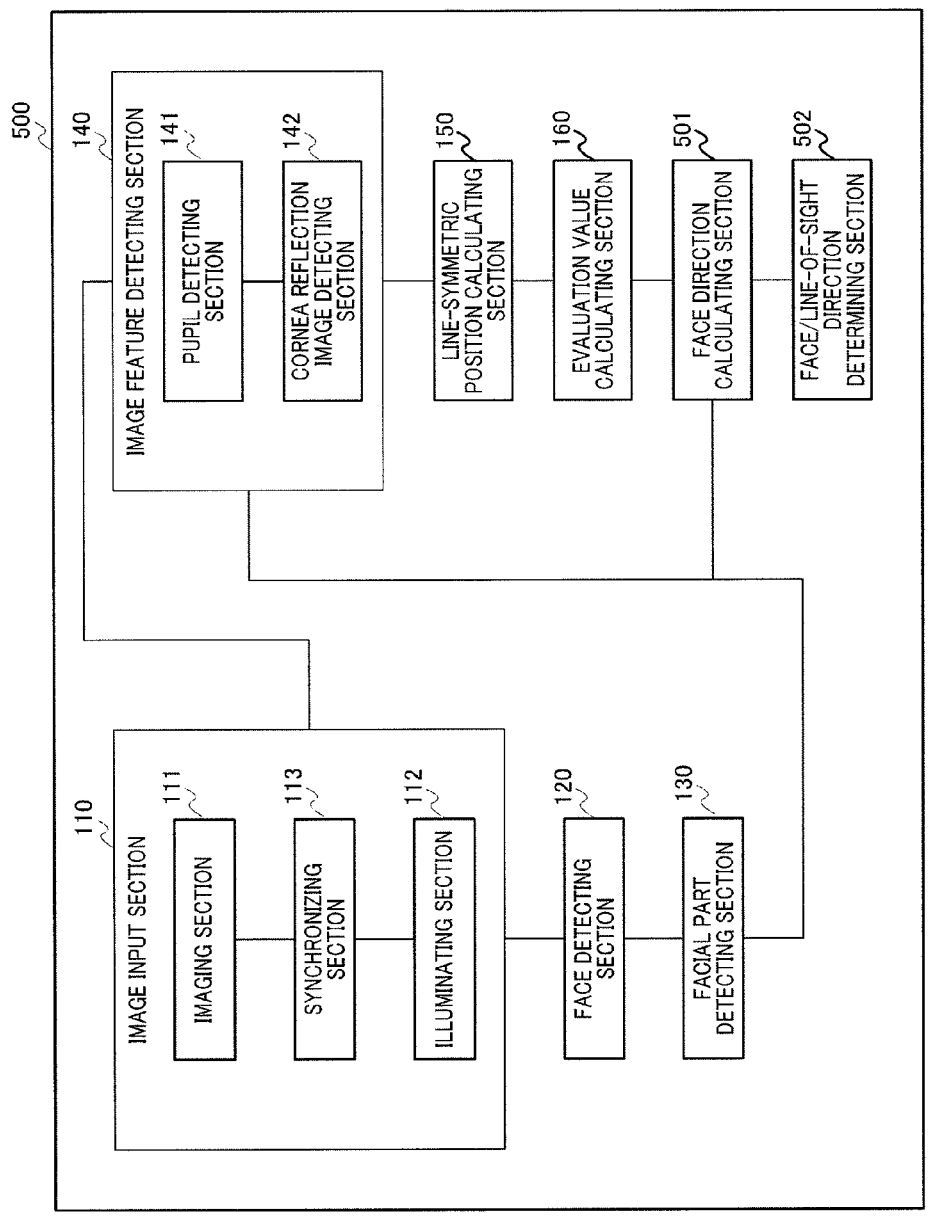
FIG. 9 is a block diagram showing a configuration of a line-of-sight direction determining apparatus according to embodiment 2 of the present invention.

FIG. 9 is a block diagram showing the configuration of the line-of-sight determining apparatus according to embodiment 2 of the present invention. In explanation of the present embodiment, the same components as in FIG. 1 will be assigned the same reference numerals without overlapping explanations.

The present embodiment is an example of applying a line-of-sight direction determining apparatus according to the present embodiment to a warning apparatus that is provided in the interior of a car, detects the direction of a driver's line of sight and issues a warning when the driver does not look at the front for a long period of time.

An example is used here where, when a face is turned in a direction of a middle point between a camera and a projector, line-of-sight direction determining apparatus 500 determines whether the line of sight is directed toward the middle point of the camera and the projector.

Line-of-sight direction determining apparatus 500 is configured with image input section 110, face detecting section 120, facial part detecting section 130, image feature detecting section 140, line-symmetric position calculating position 150, evaluation value calculating section 160, face direction calculating section 501, and face/line-of-sight determining section 502.

Face direction calculating section 501 calculates face direction information from the positions of facial parts received as input from facial part detecting section 130, and outputs the calculated information in face/line-of-sight direction determining section 502.

Face/line-of-sight direction determining section 502 continues the processing when the lateral component of the face direction information received as input from face direction calculating section 501 is directed toward a middle point between the camera and the projector, or finishes the processing when it is not. Next, face/line-of-sight direction determining section 502 determines the line symmetry of the right and left cornea reflection images from a line symmetry evaluation value received as input from evaluation value calculating section 160, determines that the direction of a subject's line of sight is directed toward a middle point direction between the camera and the projector when there is line symmetry, or determines that the direction of the subject's line of sight is not directed toward a middle point direction between the camera and the projector when there is no line symmetry, and outputs the determination result to a warning apparatus (not shown).

The operation of line-of-sight direction determining apparatus 500 configured as above will be described below.

The operation when the projector (illuminating section 112) is laterally offset from the camera (imaging section 111) will be described. The offset between the camera and the projector is substantially smaller than the distance between the camera and the face.

Figure 10:
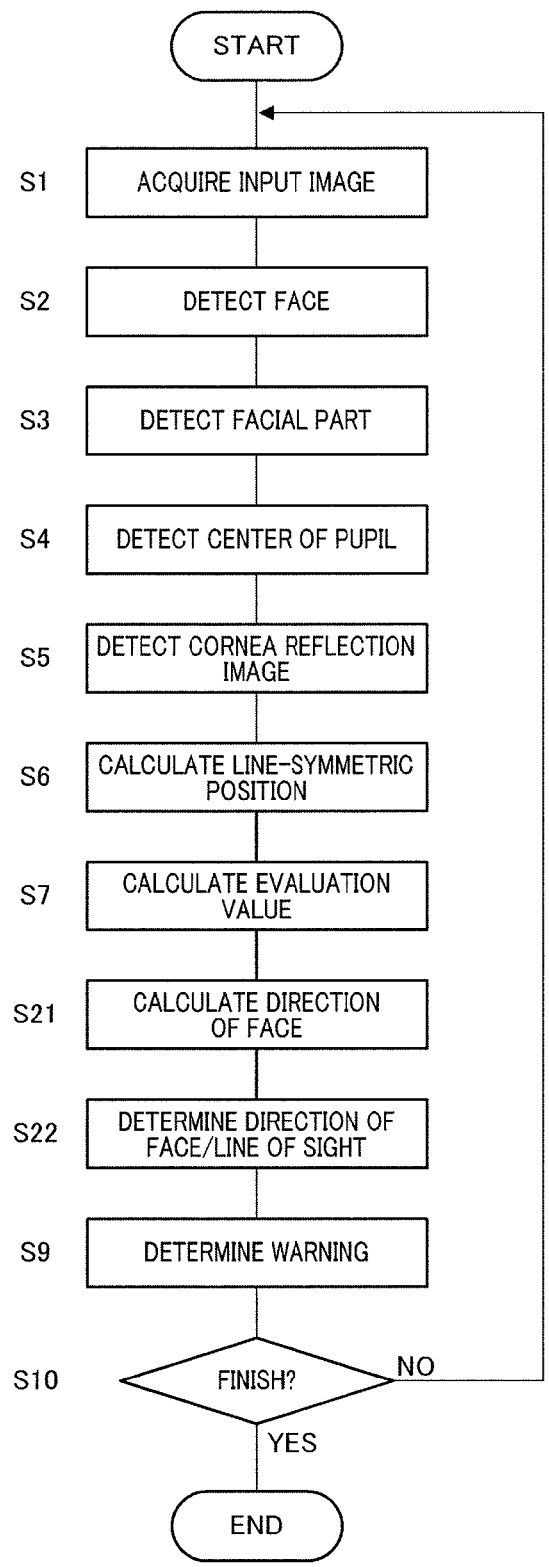
FIG. 10 is a flowchart showing a line-of-sight direction determining process of a line-of-sight direction determining apparatus according to embodiment 2.

FIG. 10 is a flowchart showing the line-of-sight direction determining process of line-of-sight direction determining apparatus 500. Parts in FIG. 6 to perform the same processes as in the flow shown in FIG. 6 are assigned the same step numbers and overlapping explanations will be explained.

In step S7, when a line symmetry evaluation value is calculated in evaluation value calculating section 160, the step moves to step S21.

In step S21, face direction calculating section 501 calculates face direction information from facial part set 302 received as input from facial part detecting section 130.

When the positions of facial parts are received as input three dimensions, for example, a normal vector of a plane on which middle points between the outer corners of the right and left eyes and the corners of the mouth are present is output as a face direction vector. When the positions of facial parts are received as input in two dimensions, for example, from the distribution of face part set 302, the posture of a regular three-dimensional head model is estimated, and a normal vector of a plane on which middle points between the outer corners of the right and left eyes and the corners of the mouth are present is acquired as a face direction vector.

In step S22, face/line-of-sight determining section 502 determines whether the face direction is directed toward a middle point between the camera and the projector from the face direction information received as input from face direction calculating section 501. The method of determination is to, for example, calculate a vector to connect between the center of the camera and the center of the projector, from the center of the camera and the center of the projector measured in advance, and determine an inner product with the lateral component of the face direction vector.

When the value of the inner product is 0, the face direction is determined to be directed toward a middle point between the camera and the projector. The value of the inner product may contain an error and does not necessarily have to be zero. When the face direction is not determined to be directed toward a middle point between the camera and the projector, the direction of line of sight is determined no to be turned in a specific direction.

Next, face/line-of-sight direction determining section 502 determines whether the direction of line of sight matches a specific direction from the line symmetry evaluation value received as input from evaluation value calculating section 160. For example, when the line symmetry evaluation value equals or exceeds a predetermined threshold, the direction of line of sight is determined to be turned in a specific direction. It is also possible to record the evaluation values over a certain period of time and determine that the direction of line of sight is turned in a specific direction when the average value equals or exceeds a threshold. The specific direction refers to, for example, the direction of a middle point between the camera and the projector.

Besides, any technology or method of determination can be used as long as the above line-of-sight direction determination is possible.

According to the present embodiment, line-of-sight direction determining apparatus 500 has face direction calculating section 501 that calculates face direction information, and face/line-of-sight direction determining section 502, and, first, when a face is directed toward a middle point between a camera and a projector (which is one example and can be any arbitrary position), determining section 502 continues the same line-of-sight direction determining process as in embodiment 1 and finishes the process when it is not. By this means, not only the direction of line of sight, the face direction also can be encompassed by the determination process. For example, it is possible to detect a driver's face looking at the front. This may be used such that, when a driver does not look at the front for a long period of time, information to that effect is output to a warning apparatus and the warning apparatus issues a warning.

(Embodiment 3)

Embodiment 3 is an application example of a line-of-sight direction determining apparatus with an auto correction function, having a function of correcting a detection error of the line-of-sight detecting apparatus automatically.

Generally speaking, when detecting the direction of a subject's line of sight from an image, the direction of line of sight is calculated using the positions of facial parts such as the outer corner of the eye, the inner corner of the eye, the eyebrow, the nostril, and the position of the pupil. However, for example, a facial part is detected off the true value or an eyeball model that is required when calculating the direction of line of sight shows a difference from the actual eyeball shape, and consequently the direction of line of sight that is detected is different from the direction a subject is really looking at, and produces a quantitative error.

A correction operation is required before measurement or during measurement in order to correct this difference of the direction of line of sight from its true value, but this operation requires, for example, fixing the head part and attentively viewing a plurality of points, and therefore is complex and places a heavy load on the subject. This is because what the subject is looking at needs to be known upon correction.

Embodiment 3 is designed to make this correction operation automatic. To be more specific, when line-of-sight direction detecting apparatuses 100 and 500 detect when the line of sight is turned in the camera's direction, and, comparing this with the detection results of line-of-sight detecting apparatuses 100 and 500 thereupon, correct the error.

Figure 11:
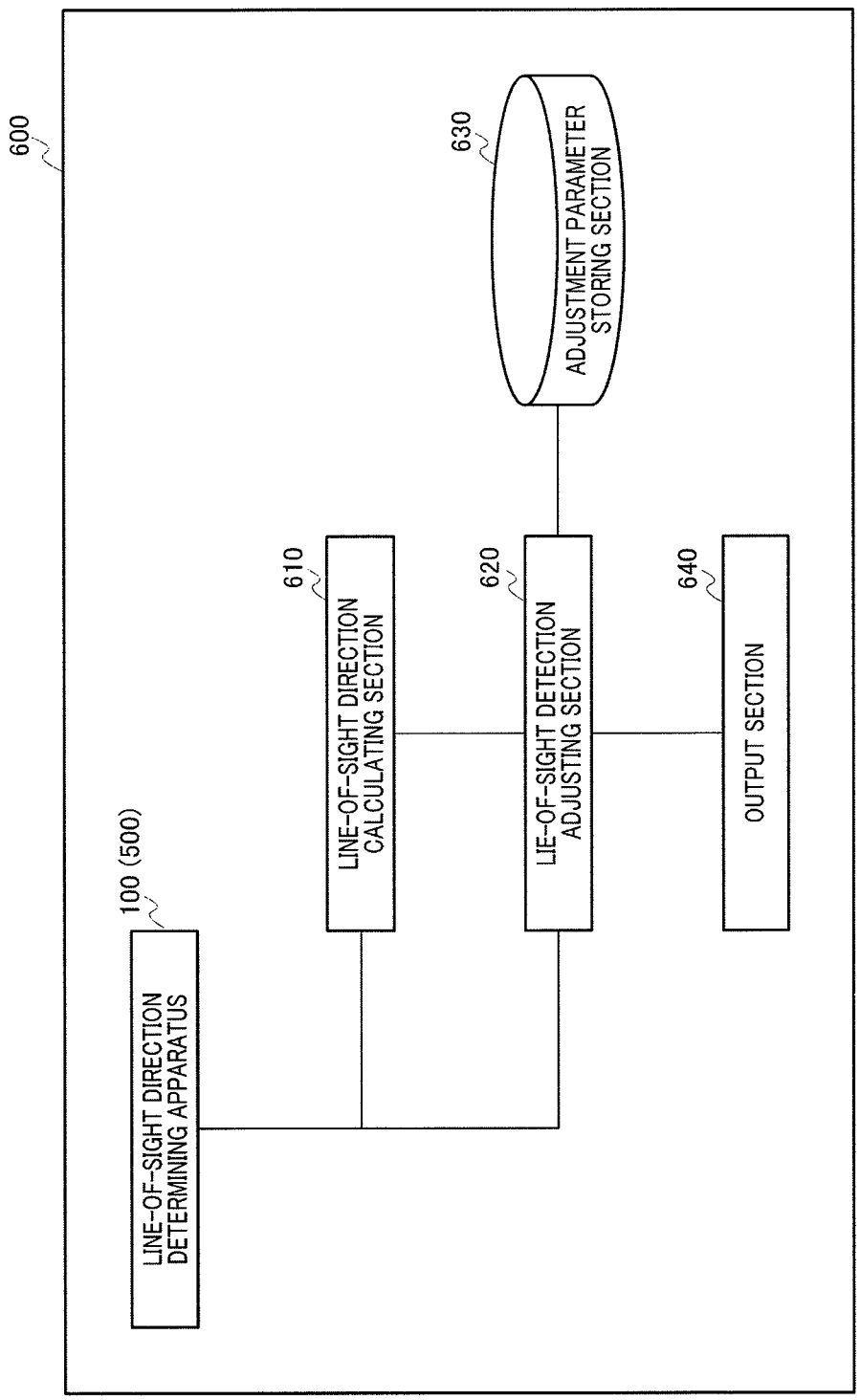
FIG. 11 is a block diagram showing a configuration of a line-of-sight direction determining apparatus with an auto correction function according to embodiment 3 of the present invention.

FIG. 11 is a block diagram showing a configuration of a line-of-sight determining apparatus with an auto correction function according to embodiment 3 of the present invention.

As shown in FIG. 11, line-of-sight direction detecting apparatus 600 with an auto correction function is configured with line-of-sight direction determining apparatus 100, line-of-sight direction calculating section 610 that calculates the direction of line-of-sight from a face image, line-of-sight detection adjusting section 620 that adjusts (corrects) the difference between a detection result of line-of-sight direction calculating section 610 and the true value, adjustment parameter storing section 630 that stores the parameters of correction results, and output section 640 that outputs line-of-sight detection results.

Although with the present embodiment line-of-sight direction determining apparatus 100 of embodiment 1 is used, it is equally possible to use line-of-sight direction determining apparatus 500 of embodiment 2 instead of line-of-sight direction determining apparatus 100.

Line-of-sight direction determining apparatus 100 determines that a direction of line of sight being turned in the direction of a camera, and acquires the detection result as line-of-sight direction determining information. Image input section 110 of line-of-sight direction determining apparatus 100 (see FIG. 1) outputs a face image to line-of-sight direction calculating section 610, and outputs line-of-sight direction determining information to line-of-sight detection adjusting section 620.

Line-of-sight direction calculating section 610 calculates the direction of line of sight from the face image received as input from image input section 110 of line-of-sight direction determining apparatus 100, and outputs line-of-sight direction information to line-of-sight detection adjusting section 620.

From the line-of-sight direction determining information received as input from line-of-sight direction determining apparatus 100 and the line-of-sight direction information received as input from line-of-sight direction calculating section 610, line-of-sight detection adjusting section 620 calculates adjustment parameter P and inputs the adjustment parameter to adjustment parameter storing section 630. From the line-of-sight direction information and adjustment parameter P received as input from line-of-sight direction calculating section 610, line-of-sight detection adjusting section 620 acquires adjusted line-of-sight direction information. Adjustment parameter P will be described using the flow of FIG. 12.

Adjustment parameter storing section 630 stores correction parameter P received as input from line-of-sight detection adjusting section 620, and outputs that adjustment parameter P to line-of-sight direction calculating section 610 via line-of-sight detection adjusting section 620.

Output section 640 outputs adjusted line-of-sight direction information received as input from line-of-sight detection correcting section 620 in the form of an image, symbol, character, and so on.

Figure 12:
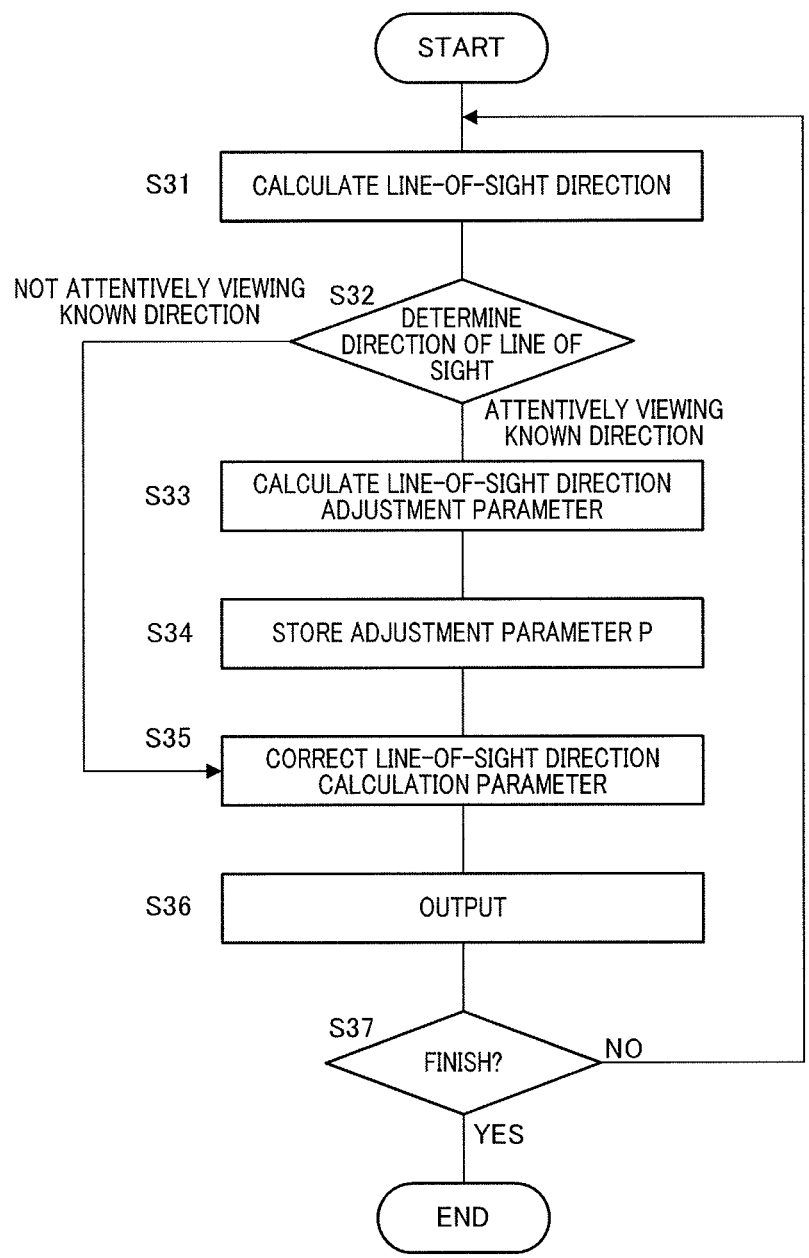
FIG. 12 is a flowchart showing operations of a line-of-sight detecting apparatus with an auto correction function according to embodiment 3.

FIG. 12 is a flowchart showing the operation of line-of-sight direction detecting apparatus 600 with an auto correction function.

When the present program starts, line-of-sight direction determining apparatus 100 starts an imaging operation. The imaging operation may be started manually by a person or may be started by a line-of-sight direction determining apparatus 100 upon being triggered by some external signal.

In step S31, line-of-sight direction calculating section 610 calculates the direction of line of sight. In this line-of-sight direction calculation, line-of-sight direction information is acquired as line-of-sight direction vector Ve. For example, the method of line-of-sight detection uses the following method. a. As in the following, in line-of-sight detection, the direction of line-of-sight is calculated from the outer corner of the eye and the inner corner of the eye detected in facial part detecting section 190 and the center of the pupil detected in pupil detecting section 141. b. First, from the positions of the outer corner of the eye and the inner corner of the eye, the center position of the eyeball is estimated. For example, the center of the eyeball is regard as being present a predetermine distance ahead in a normal direction of a line segment connecting between the outer corner of the eye and the inner corner of the eye. c. It is equally possible to use a statistic technique of measuring the position of the center of the eyeball with respect to the outer corner of the eye and the inner corner of the eye with respect to a plurality of subjects and determine an average. d. Next, a line to connect between the estimated center of the eyeball and the center of the pupil is calculated. e. Finally, a direction vector of the above line is calculated and is acquired as a line-of-sight direction vector.

Besides, any technology or method of calculation may be used as long as the above line-of-sight direction detection is possible.

In step S32, line-of-sight direction determining apparatus 100 determines whether or not the direction of line-of-sight is turned in the direction of a camera by the method shown with embodiment 1.

When the direction of line-of-sight is determined to be turned in a camera's direction, the step moves to step S33.

When the direction of line-of-sight is determined not to be turned in a camera's direction, the step moves to step S35.

In step S33, line-of-sight detection adjusting section 620 calculates adjustment parameter P for line-of-sight direction calculation. Adjustment parameter P is defined by the angle formed by line-of-sight direction vector Ve calculated in above step S31, and line-of-sight direction vector Vc when the line-of-sight is turned in the camera's direction. Adjustment parameter P is calculated by next equation 5.

(Equation 5)

$$P = \arcsin\left(\frac{\vec{V}_e \cdot \vec{V}_c}{|\vec{V}_e \cdot \vec{V}_c|}\right)$$ [5]

In step S34, adjustment parameter storing section 630 stores adjustment parameter P. Then, earlier adjustment parameters P are discarded, and the latest adjustment parameter P alone is stored.

In step S35, from adjustment parameter P, line-of-sight direction adjusting section 620 corrects line-of-sight direction information, and acquires adjusted line-of-sight direction information. Adjusted line-of-sight direction information is represented as adjusted line-of-sight direction vector Vf with the present embodiment. Adjustment of line-of-sight direction information is calculated by, for example, equation 6.

$$\vec{V}_f = \vec{V}_e \text{Rot}(P)$$ (Equation 6)

where Rot(P) is a rotation matrix rotated by an angle matching adjustment parameter P.

In step S36, output section 640 outputs adjusted line-of-sight direction information.

In step S37, a termination decision is made. A termination decision may be made manually or may be made by some automatic trigger.

If as a result of a termination decision the process is going to be finished, the line-of-sight detection adjusting operation of line-of-sight direction detecting apparatus 600 with an auto correction function is finished. If the process is not finished in above step S37, the process returns to above step S31.

The quantitative difference of the direction of line of sight from the true value can be corrected on a real time basis according to the present embodiment. Furthermore, there is an advantage of making operations that are complex and that place a heavy load on a subject unnecessary, such as fixing the head part and attentively viewing a plurality of points. This provides the following advantages.

(1) Automatic correction (adjustment) is possible without looking at a specific target to attentively view. This leads to making attentive viewing unnecessary, so that it is possible to lighten processing and prevent detection errors.

(2) More opportunities of correction are provided. Looking at a camera's direction for only one frame is sufficient, so that the likelihood is high that more opportunities for correction are provided.

Figure 13A:
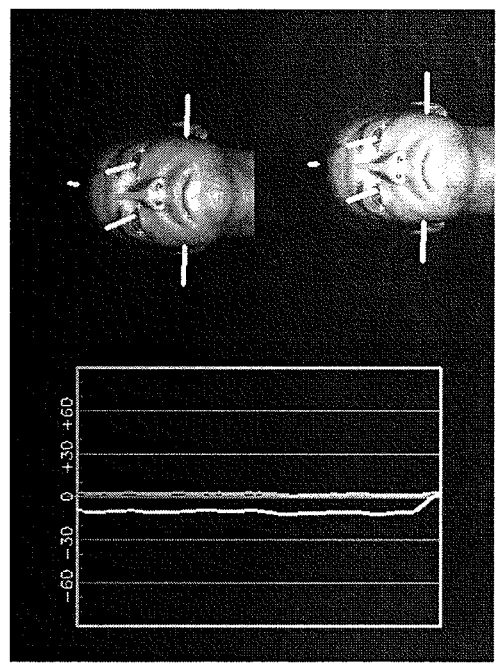
FIGS. 13A and 13B explain that a line-of-sight direction determining apparatus with an auto correction function according to embodiment 3 is able to correct offset of the direction of line of sight.
Figure 13B:
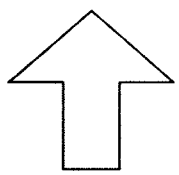
Figure 13B:
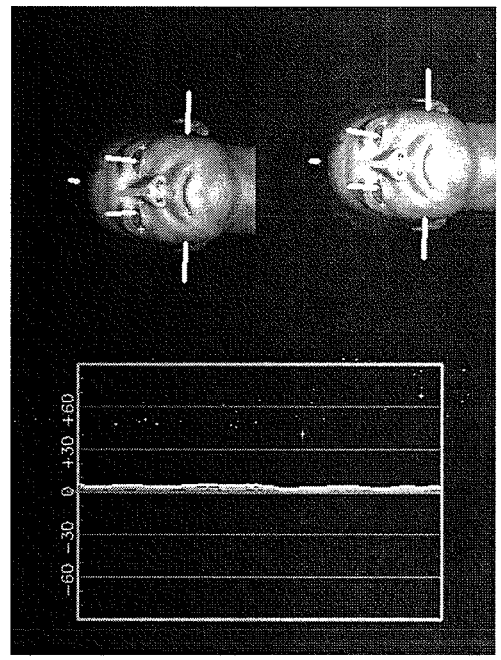

FIG. 13 explains that line-of-sight direction offset (quantitative offset from the true value) can be corrected automatically.

As shown in FIG. 13A, with a conventional line-of-sight detection technique, a quantitative offset from the true value is produced in the direction of line of sight. If the center front direction of face 202 is 0 degrees, the direction of line of sight is shifted approximately 10 degrees to the left. To correct this, it is necessary to detect "when" a specific place is looked at. However, as described as a problem to be solved, this correction is difficult. Line-of-sight direction determining apparatus 100 can acquire cornea reflection images from the right and left eyes, and detect, on a real time basis, when the direction of a projector is looked at, from the symmetry of reflected image position 205 with respect to pupil 204. By this means, as shown in FIG. 13B, it is possible to correct the offset of the direction of line-of-sight automatically and realize accurate line-of-sight detection.

(Embodiment 4)

Figure 14:
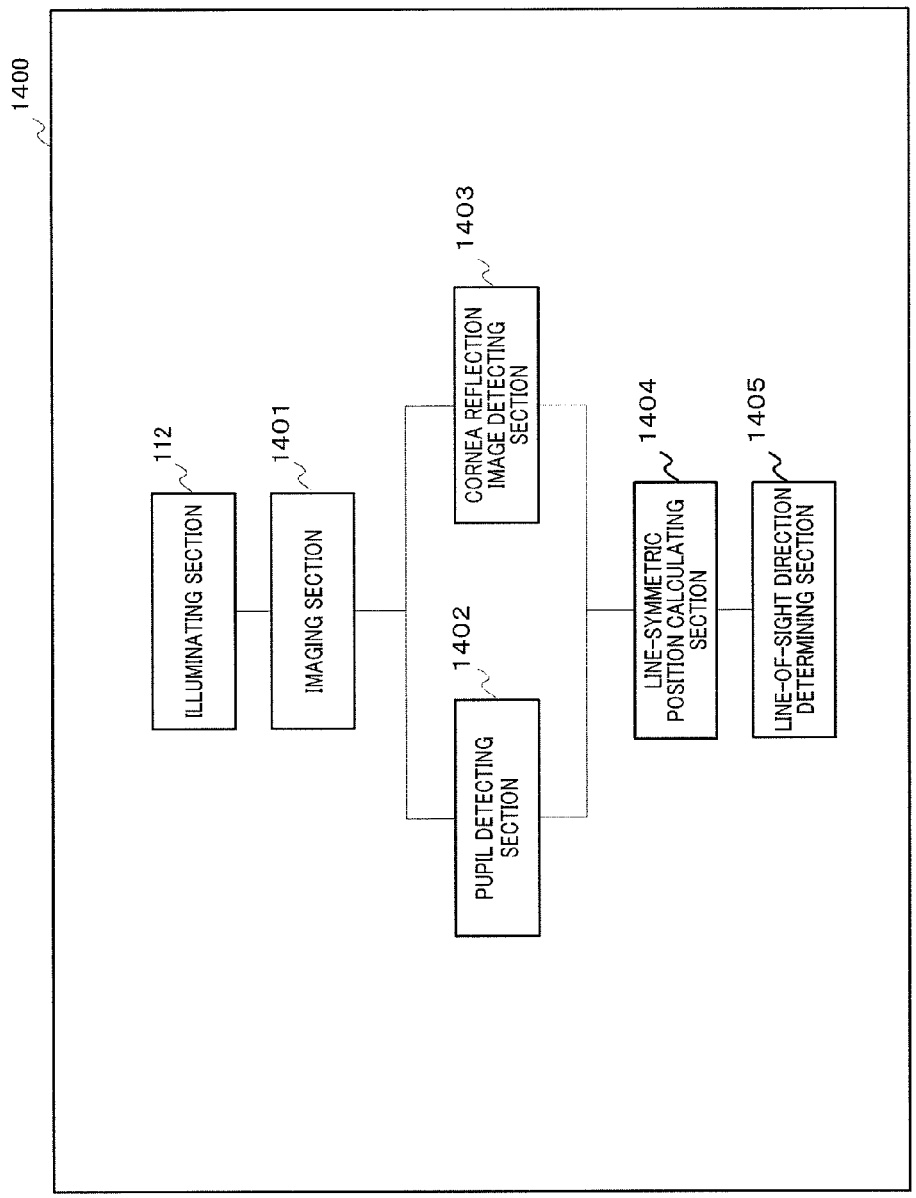
FIG. 14 is a block diagram showing a configuration of a line-of-sight direction determining apparatus according to embodiment 4 of the present invention.

FIG. 14 is a block diagram showing a configuration of a line-of-sight direction determining apparatus according to embodiment 4 of the present invention.

A face image will be described assuming that the X axis defines the lateral directions in the image, the Y axis defines the vertical directions in the image, and one pixel defines one coordinate point.

As shown in FIG. 14, line-of-sight direction determining apparatus 1400 is configured with illuminating section 112, imaging section 1401, pupil detecting section 1402, cornea reflection image detecting section 1403, line-symmetric position calculating section 1404, and line-of-sight direction determining section 1405.

Illuminating section 112 illuminates the corneas of the right and left eyes of a driver by a light source, and imaging section 1401 photographs a face image including the right and left eyes illuminated by the light source.

As explained in embodiment 1, illuminating section 112 has a light source. Illuminating section 112 emits light at least during the period from the start to end of exposure in imaging section 1401. The positional relationship between illuminating section 112 and imaging section 1401 will be described later.

Imaging section 1401 has an image sector such as CCD and CMOS, and acquires a face image including the right and left eyes. Imaging section 1401 is placed higher and in the front, or lower and in the front, with respect to a center point of a line segment between the right and left eye pupils when a driver's line of sight is in the traveling direction of a vehicle. When the driver's line of sight is in the traveling direction of a vehicle, the driver's line of sight is turned in a vertical direction of imaging section 1401.

Pupil detecting section 1402 calculates the center coordinates of the pupil based on the face image photographed in imaging section 1401, and cornea reflection image detecting section 1403 calculates the center coordinates of a cornea reflection image of the light source of illuminating section 112 in the cornea based on the face image acquired in imaging section 1401.

Based on the center coordinates of the center coordinates of the pupils of the right and left eyes and the center coordinates of the cornea reflection images in the right and left eyes, line-symmetric position calculating section 1404 calculates the coordinates of a position line-symmetric to the cornea reflection image in one of the right and left eyes, with respect to a perpendicular bisector of a line segment connecting between the center coordinates of the left eye pupil and the right eye pupil.

Line-of-sight direction determining section 1405 determines the direction of the driver's line of sight based on the distance between the center coordinates of the cornea reflection image in the other one of the right and left eyes and the coordinates of the line-symmetric position.

Next, the positional relationship between illuminating section 112 and imaging section 1401 will be explained with reference to FIG. 15.

Figure 15A:
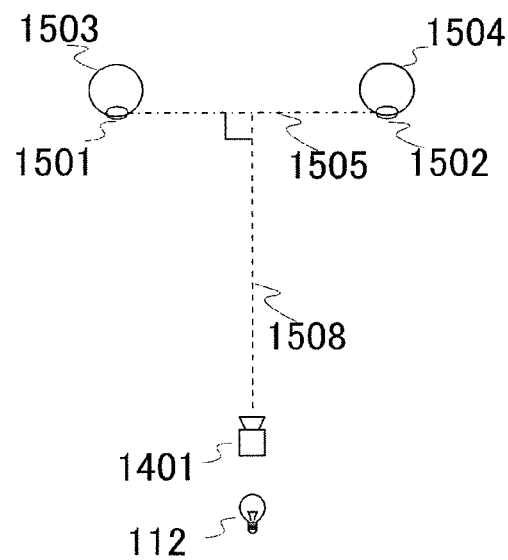
FIGS. 15A, 15B and 15C show positional relationships between an illuminating section and an imaging section in a line-of-sight direction determining apparatus according to embodiment 4.
Figure 15B:
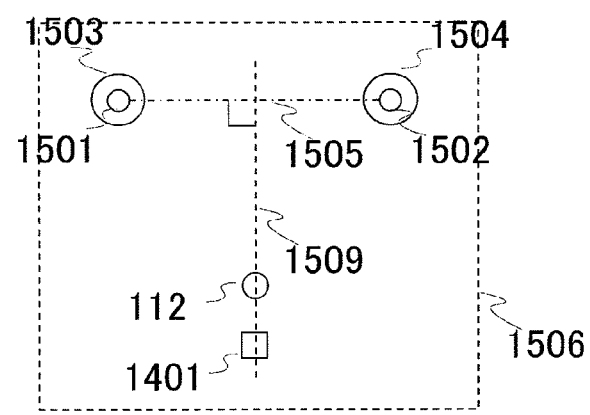
Figure 15C:
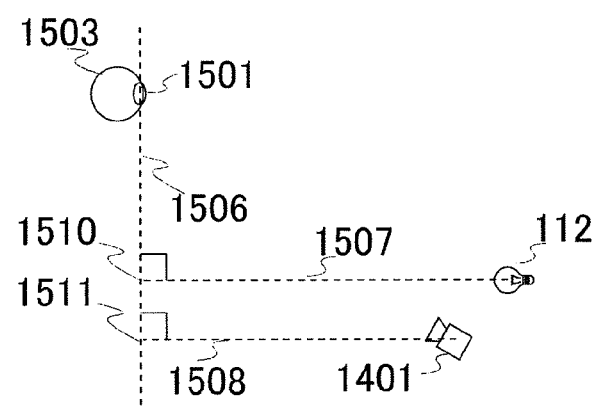

FIG. 15 shows the positional relationships between the right and left eyes, illuminating section 112 and imaging section 1401, where FIG. 15A shows a bird's-eye-view of the right and left eyes, illuminating section 112 and imaging section 1401, FIG. 15B shows a front view of the right and left eyes, and FIG. 15C shows a side view of the right and left eyes, illuminating section 112 and imaging section 1401.

FIG. 15 presumes that imaging section 1401 is in a position where imaging section 1401 can photograph the right and left eyes and illuminating section 112 and where illuminating section 112 can illuminate the corneas of the right and left eyes using a light source.

As shown in FIG. 15, given right eye pupil 1501, left eye pupil 1502, right eye eyeball 1503 and left eye eyeball 1504, line segment 1501 connecting between the center of right eye pupil 1501 and the center of left eye pupil 1502 is shown. Furthermore, plane 1506 including line segment 1505, perpendicular line 1507 from illuminating section 112 to plane 1506, perpendicular line 1508 from imaging section 1401 to plane 1506, perpendicular bisector 1509 of line segment 1505 included in plane 1506, foot 1510 of perpendicular line 1507 on plane 1506 and foot 1511 of perpendicular 1508 on plane 1506 are provided.

As shown in FIG. 15A, the angle of imaging section 1401 and illuminating section 112 is perpendicular with respect to line segment 1501 connecting between the center of right eye pupil 1501 and the center of left eye pupil 1502.

As shown in FIGS. 15B and 15C, line segment 1509 connecting between foot 1511 of perpendicular line 1508 of imaging section 1401 with respect to plane 1506 including line segment 1505, and foot 1510 of perpendicular line 1507 of illuminating section 112 with respect to plane 1506, is a perpendicular bisector of line segment 1507.

Although plane 1506 has been explained to be perpendicular with respect to right eye pupil 1501 as shown in FIG. 15C, this is by no means limiting. That is to say, plane 1506 may have an arbitrary angle with respect to a plane perpendicular to right eye pupil 1501 as long as the above relationships hold between perpendicular line 1507 and perpendicular lien 1509.

Although the distance from imaging section 1401 to line segment 1505 has been explained to be shorter than the distance from illuminating section 112 to line segment 1505 as shown in FIG. 15A, this is by no means limiting. That is to say, in the bird's-eye-view, the distance from imaging section 1401 to line segment 1505 may be the same as or longer than the distance from illuminating section 112 to line segment 1505.

Although imaging section 1401 and illuminating section 112 have been explained to be positioned low with respect to the line-of-sight direction of right eye pupil 1501, but it is equally possible to position high one of imaging section 1401 and illuminating section 112 or both.

As described above, illuminating section 112 is placed such that the line segment connecting between the foot of a perpendicular line to a plane including the line segment connecting between the pupils of the right and left eyes and imaging section 1401, and the foot of a perpendicular line from illuminating section 112 to that plane, and a line segment connecting between the pupils of the right and left eyes, cross at right angles.

Pupil detecting section 1402 detects the pupils of the right and left eyes from a face image acquired in imaging section 1401, and calculates the coordinates of the centers of the pupils of the right and left eyes. To be more specific, by applying a circle separability filter to the right and left eyes in the face image, pupil detecting section 1402 detects the circles of them maximum brightness and calculates the center coordinates of the pupils in the face image.

Cornea reflection image detecting section 1403 detects cornea reflection images of the light source of illuminating section 112 on the corneas, from the face image acquired in imaging section 1401, and calculates the center coordinates of the right and left cornea reflection images. The cornea reflection images are reflected images of the light source produced on the corneas when a light source is reflected on the corneas. To be more specific, cornea reflection image detecting section 1403 calculates a brightness histogram with respect to the face image, detects the centroid of pixels showing maximum brightness, and calculates the center coordinates of the cornea reflection images.

The centroid of pixels showing maximum brightness is determined by extracting a pixel having brightness equal to or greater than a predetermined value, and by using the coordinates of that pixel as centroid. The above predetermined value may be determined on a dynamic basis so that the number of pixels having brightness equal to or greater than a predetermined value is equals or exceeds a predetermined number in the brightness histogram or may be a predetermined value.

The coordinate average upon the calculation of centroid may be a simple average or a weighted average using brightness as weight.

Line-symmetric position calculating section 1404 receives the center coordinates of the pupils of the right and left eyes from pupil detecting section 1403 and receives the center coordinates of the cornea reflection images of the right and left eyes from cornea reflection image detecting section 1404. Then, line-symmetric position calculating section 1404 calculates a perpendicular bisector of a line segment connecting between the center coordinates of the left eye pupil and the center coordinates of the right eye pupil, and calculates the coordinates of a position that is line-symmetric to the cornea reflection image in one of the right and left eyes with respect to the perpendicular bisector.

Figure 16A:
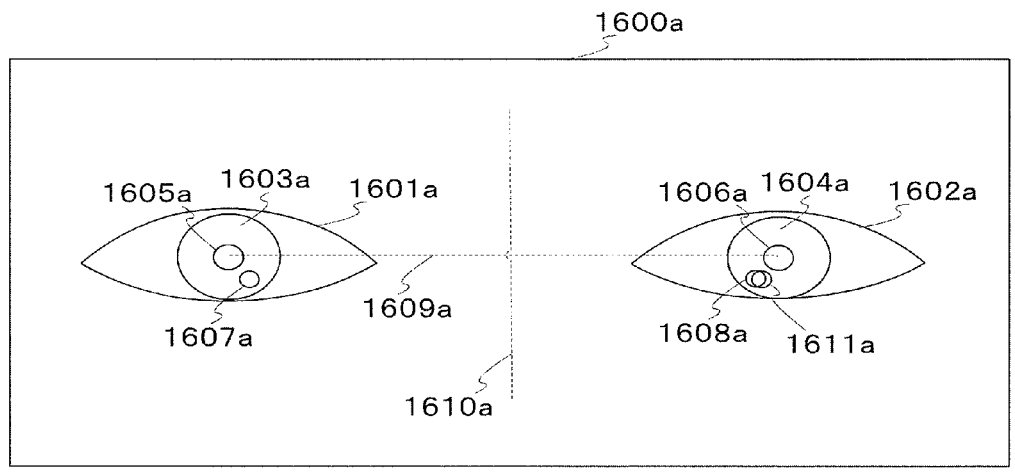
FIGS. 16A and 16B show positional relationships between a cornea reflection image and a cornea-projected image, by a line-of-sight direction determining apparatus according to embodiment 4.
Figure 16B:
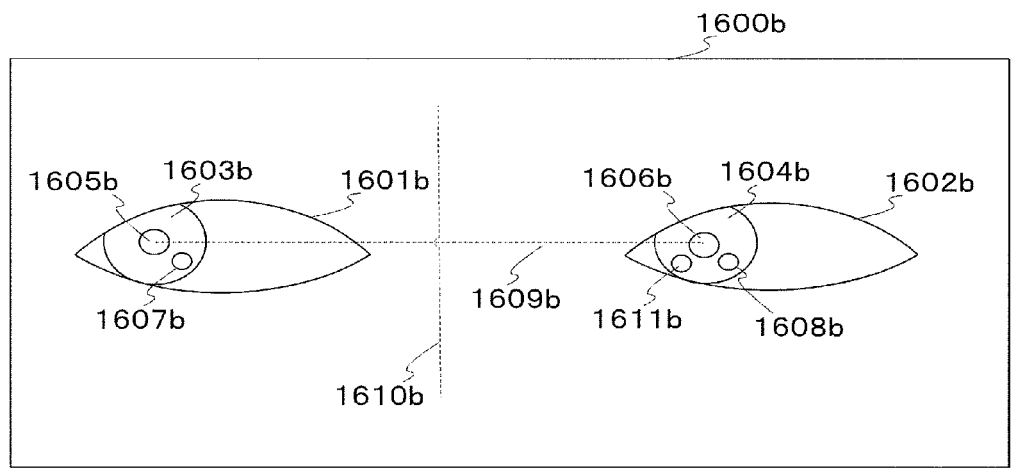

FIG. 16 shows positional relationships between cornea reflection images and cornea-projected images, FIG. 16A is a front view of the right and left eyes in a face image when the line of sight is turned in a vertical direction of imaging section 1401 (FIG. 14), and FIG. 16B is a front view of the right and left eyes in a face image when the line of sight is turned in a lateral direction of imaging section 1401.

As shown in FIG. 16A, face image 1600 including the right and left eyes, right eye 1601, left eye 1602, right eye cornea 1603, left eye cornea 1604, right eye pupil 1605, left eye pupil 1606, right eye cornea reflection image 1607, left eye cornea reflection image 1608, line segment 1609 connecting between right eye pupil and the left eye pupil, perpendicular bisector 1610 of line segment 1609, and cornea-projected image 1611.

As shown in FIG. 16A, when the line of sight is turned in a vertical direction of imaging section 1401 (FIG. 14), the light source in illuminating section 112 (FIG. 14) illuminates the corneas of the right and left eyes from the front, so that right eye cornea reflection image 1607a is projected on the inner side of the face with respect to right eye pupil 1605a, and left eye cornea reflection image 1608a is projected on the inner side of the face with respect to left eye pupil 1606a.

Line-symmetric position calculating section 1404 draws line segment 1609a based on right eye pupil 1605a and left eye pupil 1606a, and calculates perpendicular bisector 1610a of line segment 1609a.

Then, line-symmetric position calculating section 1404 calculates a coordinate point in a position line-symmetric to right eye cornea reflection image 1607a with respect to perpendicular bisector 1610a. The above coordinate point defined as a cornea-projected image.

Now, as shown in FIG. 16A, when the line of sight is turned in a vertical direction of imaging section 1401, the light source of illuminating section 112 illuminates the corneas of the right and left eyes from the front, right eye cornea reflection image 1607a and left eye cornea reflection image 1608a are line-symmetric with respect to perpendicular bisector 1610a. Consequently, under the condition the corneas of the right and left eyes have the same shape, cornea reflection image 1611a and left eye cornea reflection image 1608a are the same coordinates.

Even when the line of sight is turned in a lateral direction with respect to a vertical direction of imaging section 1401 as shown in FIG. 16B, cornea-projected image 1611b is calculated by performing the same processing as the processing having been described using FIG. 16A.

Now, as shown in FIG. 16B, if the line of sight turns in a lateral direction with respect to a vertical direction of imaging section 1401, the light source of illuminating section 112 illuminates the corneas of the right and left eyes from a lateral direction, and therefore right eye cornea reflection image 1607b and left eye cornea reflection image 1608b do not become line-symmetric with respect to perpendicular bisector 1610b. Consequently, a distance is produced between the coordinate points of cornea-projected image 1611b and the coordinate points of left eye cornea reflection image 1608b, and the distance becomes greater as the line of sight drifts farther from a vertical direction.

The functions of line-of-sight direction determining section 1405 based on the relationship between the direction of line of sight and the distance between cornea reflection image 1608b and cornea-projected image 1611b described above.

Although coordinate points in a line-symmetric position to right eye cornea reflection image 1607a with respect to perpendicular bisector 1610a are calculated as a cornea-projected image here, it is equally possible to calculate a coordinate point in a position line-symmetric to left eye cornea reflection image 1608a with respect to perpendicular bisector 1610a, as a cornea-projected image. In this case, in line-of-sight direction determining section 1405 (described later), the direction of line of sight is determined based on the distance between the coordinate points of the cornea-projected image and the coordinate points of the right eye cornea reflection image.

Line-of-sight direction determining section 1405 calculates the distance between the coordinate points of cornea-projected image 1611 calculated in line-symmetric position calculating section 1404, and the cornea reflection image present together with cornea reflection image 1611 in the same cornea, compares the distance with a predetermined threshold, and, by this means, determines the direction of line of sight.

As shown in FIG. 16, when the line of sight is turned in a vertical direction of imaging section 1401, the cornea-projected image in one eye and the cornea reflection image in the other eye are present in the same coordinate points or in neighboring coordinate points.

On the other hand, when the line of sight is turned in a lateral direction with respect to a vertical direction of imaging section 1401, the cornea-projected image in one eye and the cornea reflection image in the other eye become distant apart.

Consequently, when the distance between a cornea-projected image in one eye and a cornea reflection image in the other eye in a face image is less than a predetermined distance, it is possible to determine that the line of sight is turned in a vertical direction of imaging section 1401 or in a lateral direction near a vertical direction, or, when the distance between a cornea-projected image in one eye and a cornea reflection image in the other eye is greater than a predetermined distance, it is possible to determine that the line of sight is turned in a vertical direction of imaging section 1401 or in a lateral direction near a vertical direction.

Based on the above principles, line-of-sight determining section 1405 calculates the distance between the coordinate points of the cornea-projected image 1611a and the coordinate points of cornea reflection image 1608, compares the distance with a predetermined threshold, and, by this means, determines the direction of line of sight.

The predetermined threshold is determined based on facial parts including the shape of the cornea, and needs to be set taking into account the uniqueness of the driver.

Although in the above descriptions the direction of line of sight is determined by calculating the distance between the coordinate points of cornea-projected image 1611a and the coordinate points of cornea reflection image 1608a, it is equally possible to provide an evaluation value calculating section as explained in embodiment 1.

Figure 17:
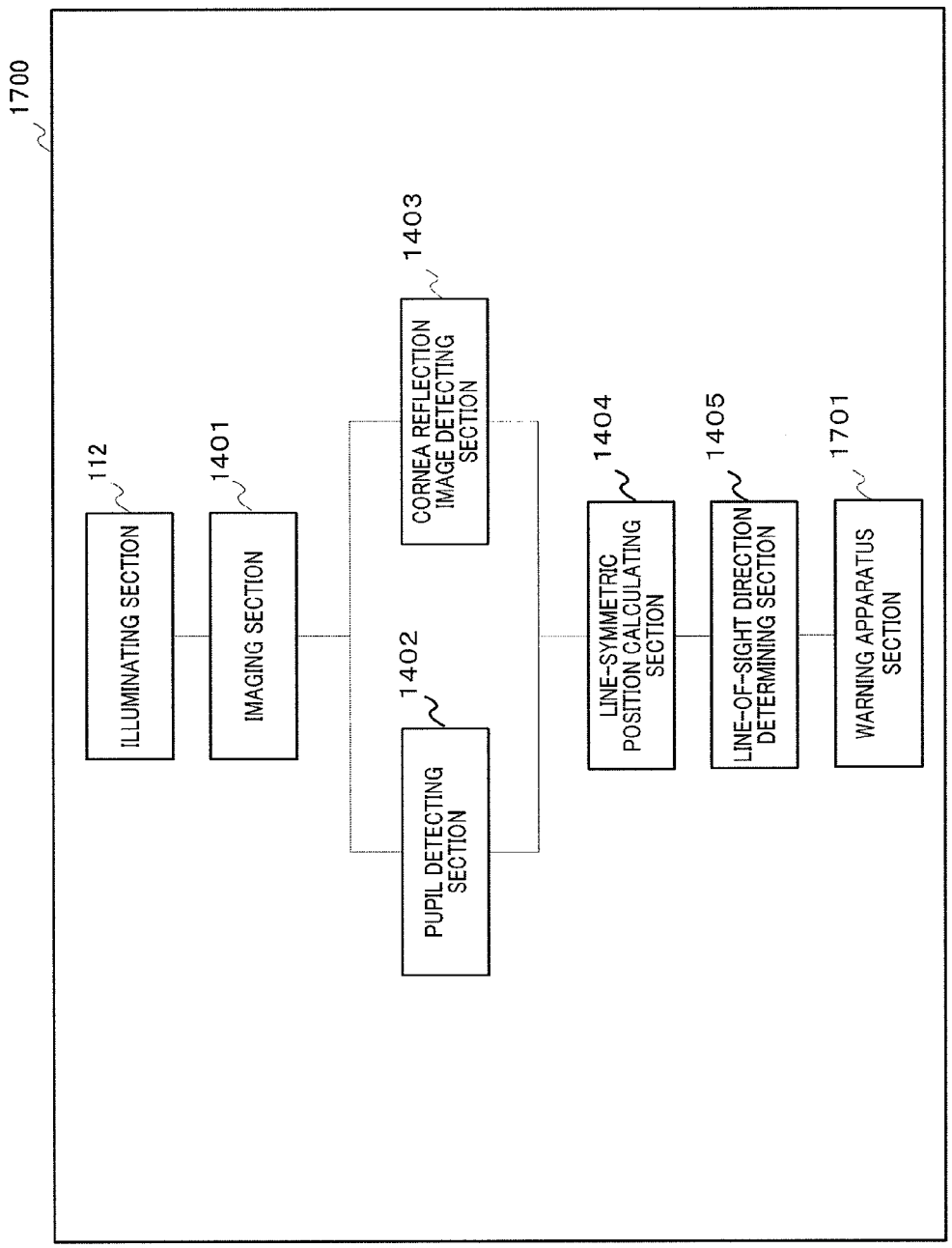
FIG. 17 is a block diagram showing a configuration of a line-of-sight direction determining apparatus with a warning apparatus section according to embodiment 4.

It is equally possible to adopt a configuration further comprising warning apparatus section n1701, as shown in FIG. 17, as explained in embodiment 1. FIG. 17 is a block diagram showing a configuration of line-of-sight direction determining apparatus 1700 having warning apparatus section 1701. If the line of sight is determined not to be turned in a front direction and the count of the number of times the line of sight is determined not to be turned in a front direction exceeds a predetermined threshold, N, exceeds a predetermined threshold, warning apparatus section 1710 decides that the line of sight has not looked at the front for a long period of time and issues a warning.

Preferred embodiments of the present invention in the above descriptions have only been described by way of example and by no means limit the scope of the invention. Although a warning apparatus has been described above with the present embodiment that is provided in the interior of a car, detects the direction of a driver's line of sight and issues a warning if the driver does not look at the front for a long period of time, this is applicable to any apparatus as long as it is an electrical device having a line-of-sight determining apparatus for determining the direction of line-of-sight.

For example, application to a device to present information such as a television and speaker, a device to monitor safety conditions such as a surveillance camera, a device to record images such as a still camera and a video camera, a life-assistance device such as a robot, and an entertainment/recreation device such as a TV game and virtual game. Application to the above devices provides an advantage that, unlike the prior art, it is not necessary to perform adjustment in advance on a per individual basis, and it is possible to determine the direction of line of sight reliably.

The warning apparatus according to the above embodiments can be realized by substituting an image recording means for recording an input image, a surrounding information learning means for allowing a robot to learn the condition of a user or robot, a condition updating means for changing the condition of a game.

The line-symmetric position calculating method according to the above embodiments is only an example and can be replaced by various calculation methods. Furthermore, the method of line symmetry evaluation value calculation may use other calculation methods as well. In an experiment by the present inventors, a good result was achieved by the method of calculating an evaluation value based on the distance between the center of a cornea reflection image of an eye corresponding to a line-symmetric position.

The present embodiment uses the terms "line-of-sight direction determining apparatus" and "line-of-sight direction determining method" have been used for ease of explanation, the apparatus may be a "line-of-sight detecting apparatus" and the method may be "line-of-sight direction determining method."

The components to constitute the above line-of-sight direction determining apparatus, the types of the face detecting section, the method of facial part detection, and further the types of image feature detecting section are not limited to the above embodiments described above.

The line-of-sight direction determining apparatus described above is implemented by a program for making a line-of-sight direction determining method. This program is stored in a computer-readable recording medium.

The disclosure of Japanese Patent Application No. 2008-248877, filed on Sep. 26, 2008, including the specification, drawings, and abstract are incorporated herein by reference in its entirety,

INDUSTRIAL APPLICABILITY

The line-of-sight direction determining apparatus and line-of-sight direction determining method according to the present invention are suitable for use as an information terminal such as a personal computer, OA electronics, mobile telephone, etc., and an information providing apparatus provided as a mobile means such as a car, airplane, ship, train, etc. Furthermore application for use to surveillance and warning apparatus, robot, and image/audio playback apparatus.

REFERENCE SIGNS LIST 100 and 500,1400,1700 Line-of-sight direction determining apparatus
110 Image input section
111 Imaging section
112 Illuminating section
113 Synchronizing section
120 Face detecting section
130 Facial part detecting section
140 Image feature detecting section
141 Pupil detecting section
142 Cornea reflection image detecting section
150 Line-symmetric position calculating section
160 Evaluation value calculating section
170 Line-of-sight direction determining section
501 Face direction calculating section
502 Face/line-of-sight determining section
600 Line-of-sight direction detecting apparatus with auto correction function
610 Line-of-sight calculating section
620 Line-of-sight detection correcting section
630 Adjustment parameter storing section 630
640 Output section
1400 Line-of-sight direction determining apparatus
1401 Imaging section
1402 Pupil detecting section
1403 Cornea reflection image detecting section
1404 line-symmetric position calculating section
1405 Line-of-sight direction determining section
1501 Right eye pupil
1502 Left eye pupil
1503 Right eye eyeball
1504 Left eye eyeball
1505 Line segment connecting between right eye pupil center and left eye pupil center
1506 Plane
1507 Perpendicular line
1508 Perpendicular line 1509 Perpendicular bisector
1510 Foot of perpendicular line
1511 Foot of perpendicular line
1600 Face image
1601 Right eye
1602 Left eye
1603 Right eye cornea
1604 Left eye cornea
1605 Right eye pupil
1606 Left eye pupil
1607 Right eye cornea reflection image
1608 Left eye cornea reflection image
1609 Line segment
1610 Perpendicular bisector
1611 Cornea-projected image
1700 Line-of-sight direction determining apparatus
1701 Warning apparatus section

The invention claimed is:

1. A line-of-sight direction determining apparatus comprising:
   an imaging section that takes an image of a face including right and left eyes;
   an illuminating section that illuminates corneas of the right and left eyes using a light source;
   a pupil detecting section that detects a first coordinate and a second coordinate, the first coordinate and the second coordinate being a center coordinate of the pupil of one of the right and left eyes and a center coordinate of the pupil of the other one of the right and left eyes, respectively;
   a cornea reflection image detecting section that detects a third coordinate and a fourth coordinate, the third coordinate and the fourth coordinate being a center coordinate of a cornea reflection image of the light source on the cornea of one of the right and left eyes and a center coordinate of a cornea reflection image of the light source on the cornea of the other one of the right and left eyes, respectively;
   a line-symmetric position calculating section that calculates a perpendicular bisector of a first line segment connecting between the first coordinate and the second coordinate, and calculates a line-symmetric position coordinate being a position coordinate that is line-symmetric to the third coordinate with respect to the perpendicular bisector; and
   a line-of-sight direction determining section that calculates a coordinate distance between the fourth coordinate and the line-symmetric position coordinate, and, based on a comparison of the coordinate distance and a predetermined threshold, determines a direction of line of sight of the right and left eyes.

2. The line-of-sight direction determining apparatus according to claim 1, wherein a second line segment connecting between a foot of a perpendicular line from the imaging section to a plane including the first line segment and a foot of a perpendicular line from the illuminating section to the plane, and the first line segment cross at right angles.

3. The line-of-sight direction determining apparatus according to claim 1, further comprising a warning apparatus, wherein the warning apparatus receives determination results in the line-of-sight determining section, counts the number of times the direction of line of sight is determined not to match a specific direction, and issues a warning when the count of the number of times exceeds a predetermined number of times.

4. The line-of-sight direction determining apparatus according to claim 3, wherein the warning apparatus makes the count of the number of times zero upon receiving a determination result that the direction of line of sight matches the specific direction.

5. The line-of-sight determining apparatus according to claim 1, further comprising:
   a face direction calculating section that determines a direction of the face based on the image of the face; and
   a face/line-of-sight direction determining section that determines a direction of line of sight based on the coordinate distance and the predetermined threshold, when the face direction calculating section determines that the direction of the face matches the specific direction,
   wherein the line-of-sight direction determining section determine the direction of line of sight using the direction of the face as a parameter.

6. The line-of-sight direction determining apparatus according to claim 1, further comprising:
   a line-of-sight direction calculating section that calculates line-of-sight direction information from the image of the face acquired in the imaging section; and
   an adjusting section that calculates an offset value of the direction of line of sight based on a determination result in the line-of-sight direction determining section and the line-of-sight direction calculation information, and adjusts the direction of line of sight based on the offset value.

7. A line-of-sight direction determining method comprising:
   taking an image of a face including right and left eyes,
   illuminating corneas of the right and left eyes using a light source,
   detecting a first coordinate and a second coordinate, the first coordinate and the second coordinate being a center coordinate of the pupil of one of the right and left eyes and a center coordinate of the pupil of the other one of the right and left eyes, respectively;
   detecting a third coordinate and a fourth coordinate, the third coordinate and the fourth coordinate being a center coordinate of a cornea reflection image of the light source on the cornea of one of the right and left eyes and a center coordinate of a cornea reflection image of the light source on the cornea of the other one of the right and left eyes, respectively;
   calculating a perpendicular bisector of a first line segment connecting between the first coordinate and the second coordinate, and calculating a line-symmetric position coordinate being a position coordinate that is line-symmetric to the third coordinate with respect to the perpendicular bisector; and
   calculating a coordinate distance between the fourth coordinate and the line-symmetric position coordinate, and, based on a comparison of the coordinate distance and a predetermined threshold, determining a direction of line of sight of the right and left eyes.

* * * * *